(12) United States Patent (10) Patent No.: US 7,738,086 B2
Shepard et al. (45) Date of Patent: Jun. 15, 2010

(54) ACTIVE CMOS BIOSENSOR CHIP FOR FLUORESCENT-BASED DETECTION

(75) Inventors: Kenneth L. Shepard, Ossining, NY (US); Rastislav Levicky, Irvington, NY (US); George Patounakis, North Brunswick, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 398 days.

(21) Appl. No.: 11/800,468

(22) Filed: May 4, 2007

(65) Prior Publication Data

US 2008/0037008 A1 Feb. 14, 2008

Related U.S. Application Data

(63) Continuation-in-part of application No. 11/431,405, filed on May 9, 2006, now abandoned.

(60) Provisional application No. 60/679,545, filed on May 9, 2005, provisional application No. 60/799,408, filed on May 9, 2006.

(51) Int. Cl.
*G01N 21/00* (2006.01)
(52) U.S. Cl. .......................... 356/73; 356/317; 356/318; 436/172; 435/4; 435/6
(58) Field of Classification Search .................. 356/73, 356/244, 246, 317, 318; 435/4, 6; 436/172; 422/82.08
See application file for complete search history.

(56) References Cited

U.S. PATENT DOCUMENTS

| | | | |
|---|---|---|---|
| 5,039,219 | A | 8/1991 | James et al. |
| 5,812,272 | A | 9/1998 | King et al. |
| 6,078,705 | A | 6/2000 | Neuschafer et al. |
| 6,117,643 | A | 9/2000 | Simpson et al. |
| 6,197,503 | B1 | 3/2001 | Vo-Dinh et al. |
| 6,317,207 | B2 | 11/2001 | French et al. |

(Continued)

OTHER PUBLICATIONS

Schena, M. et al., "Microarrays: biotechnology's discovery platform for functional genomics," Trends in Biotechnology, vol. 16, pp. 301-306, Jul. 1998.

(Continued)

*Primary Examiner*—L. G Lauchman
(74) *Attorney, Agent, or Firm*—Wilmer Cutler Pickering Hale and Dorr

(57) ABSTRACT

An active CMOS biosensor chip for fluorescent-based detection is provided that enables time-gated, time-resolved fluorescence spectroscopy. In one embodiment, analytes are loaded with fluorophores that are bound to probe molecules immobilized on the surface of the chip. Photodiodes and other circuitry in the chip are used to measure the fluorescent intensity of the fluorophore at different times. These measurements are then averaged to generate a representation of the transient fluorescent decay response unique to the fluorophores. In addition to its low-cost, compact form, the biosensor chip provides capabilities beyond those of macroscopic instrumentation by enabling time-gated operation for background rejection, easing requirements on optical filters, and by characterizing fluorescence lifetime, allowing for a more detailed characterization of fluorophore labels and their environment. The biosensor chip can be used for a variety of applications including biological, medical, in-the-field applications, and fluorescent lifetime imaging applications.

26 Claims, 16 Drawing Sheets

U.S. PATENT DOCUMENTS

| | | | |
|---|---|---|---|
| 6,331,438 | B1 | 12/2001 | Aylott et al. |
| 6,448,064 | B1 | 9/2002 | Vo-Dinh et al. |
| 6,469,785 | B1 | 10/2002 | Duveneck et al. |
| 6,743,581 | B1 | 6/2004 | Vo-Dinh |
| 6,784,982 | B1 | 8/2004 | Blumenfeld et al. |
| 6,803,238 | B1 | 10/2004 | Eggers |
| 6,867,851 | B2 | 3/2005 | Blumenfeld et al. |
| 6,975,251 | B2 | 12/2005 | Pavicic |
| 7,145,645 | B2 | 12/2006 | Blumenfeld et al. |
| 7,179,654 | B2 | 2/2007 | Verdonk et al. |
| 2003/0143575 | A1 | 7/2003 | Caria |
| 2004/0175821 | A1 | 9/2004 | Ehman |
| 2004/0234417 | A1 | 11/2004 | Schienle et al. |
| 2004/0249227 | A1 | 12/2004 | Klapproth et al. |
| 2005/0136448 | A1 | 6/2005 | Hartel et al. |
| 2006/0014151 | A1 | 1/2006 | Ogura et al. |
| 2006/0134644 | A1 | 6/2006 | Hartel et al. |
| 2006/0197960 | A1 | 9/2006 | Bazylenko |
| 2007/0121111 | A1 | 5/2007 | Blumenfeld et al. |
| 2008/0265177 | A1* | 10/2008 | Connally et al. ......... 250/461.2 |

OTHER PUBLICATIONS

Daubert, S.J. et al., "Current Copier Cells," Electronic Letters, vol. 24, No. 25, pp. 1560-1562, Dec. 8, 1988.

Mir, K.U. et al., "Sequence Variation in Genes and Genomic DNA: Methods for Large-Scale Analysis," Annu. Rev. Genomics Hum, Genet. 2000. 1:329-60.

McIntosh, S.L., et al., "Fluorescence Lifetime for On-the-Fly Multiple Detection of DNA Restriction Fragments in Capillary Electrophoresis," Analytical Chemistry, vol. 72, No. 1, pp. 5444-5449, Nov. 1, 2000.

Templin, M.T. et al., "Protein microarray technology," Trends in Biotechnology, vol. 20, No. 4, pp. 160-166, Apr. 2002.

Daubert, S.J. et al., "A Transistor-Only Current-Mode $\Sigma\Delta$ Modulator," IEEE Journal of Solid-State Circuits, vol. 27, No. 5, pp. 821-830, May 1992.

Hacia, J.G. et al., "Mutational analysis using oligonucleotide microarrays," J. Med. Genet, pp. 730-736, 1999.

Hyun, D. et al., "Limit Cycles and Pattern Noise in Single-Stage Single-Bit Delta-Sigma Modulators," IEEE Transactions on Circuits and Systems—I: Fundamental Theory and Applications, vol. 49, No. 5, pp. 646-656, May 2002.

Eltoukhy, H. et al., "A 0.18 μm CMOS $10^{-5}$lux Bioluminescence Detection System-on-Chip," ISSCC 2004 / Session 12 / Biomicrosystems / 12.3, pp. 1-3.

* cited by examiner

SIMULATED READ NOISE SUMMARY.

| Item | Input Referred Noise |
|---|---|
| Reset noise ($\overline{V^2_{n,reset}}$) | $6.776 \times 10^{-11}\ V^2$ |
| Pixel transconductor noise ($\overline{V^2_{n,pixgm}}$) | $2.915 \times 10^{-10}\ V^2$ |
| Current-mode SH noise ($\overline{V^2_{n,currsh}}$) | $2.046 \times 10^{-9}\ V^2$ |
| Quantization noise ($\overline{V^2_{n,quant}}$) | $4.930 \times 10^{-10}\ V^2$ |
| Total | $2.898 \times 10^{-9}\ V^2$ ($3.74 \times 10^8\ \frac{photons}{cm^2}$) |

FIG. 18

CHIP SPECIFICATIONS AND MEASURED PERFORMANCE

| Item | Value |
|---|---|
| Chip | |
| Technology | TSMC 0.25 $\mu m$ Mixed-Signal CMOS |
| Die Size | 5 mm × 5 mm |
| Clock Speed | 20 MHz |
| SRAM Size | 2048×24-bits |
| Sensitivity | $1.15 \times 10^8$ $photons/cm^2$ |
| Linearity | 9 bits (w/o calibration) |
| Delay line resolution | 230 ps |
| Laser drive maximum current (at 2.7 V) | 130 mA |
| Time to complete single measurement | 33 ms |
| Pixel array | |
| Array size | 8 × 4 |
| Quantum efficiency (at 635 nm) | 0.45 |
| Pixel size | 180 × 415 $\mu m^2$ |
| Photodiode size | 100 × 100 $\mu m^2$ |
| Transconductor gain | 0.22 $mS$ |
| Pixel gain | 7.04 $\times 10^{-7} \mu A/e$ |
| Dark signal | 10.4 $\mu A/s$ |
| $\tau_{diode}$ | 1.2 ns |
| $R_{diode}$ | 1.4 k$\Omega$ |
| ADC | |
| Architecture | Current Mode $\Sigma\Delta$ |
| Order | 2 |
| DAC | 1-bit Differential |
| ADC gain | $205 DN/\mu A$ |
| Cycle Time | 8 $\mu s$ (>12-bit settling) |
| Cycles per Sample | 4096 (adjustable) |
| Input full scale | ±10 $\mu A$ |

FIG. 19

ACTIVE CMOS BIOSENSOR CHIP FOR FLUORESCENT-BASED DETECTION

CROSS-REFERENCE TO RELATED APPLICATION

This application is a continuation-in-part of U.S. patent application Ser. No. 11/431,405, filed May 9, 2006, which claims the benefit under 35 U.S.C. §119(e) of U.S. Provisional Patent Application No. 60/679,545, filed May 9, 2005, which are hereby incorporated by reference herein in its entirety. This application also claims the benefit under 35 U.S.C. §119(e) of U.S. Provisional Patent Application No. 60/799,408, filed May 9, 2006, which is hereby incorporated by reference herein in its entirety.

STATEMENT REGARDING FEDERALLY SPONSORED RESEARCH

This invention was made with United States Government support under National Science Foundation Grant No. BES-0428544 and National Institutes of Health Grant No. HG003089. The United States Government may have certain rights in this invention.

BACKGROUND OF THE INVENTION

1. Technical Field

The present invention relates to fluorescent-based detection. More particularly, the present invention relates to systems and methods for providing time-gated, time-resolved fluorescent-based detection on an active complementary metal oxide semiconductor (CMOS) biosensor chip.

2. Description of the Related Art

An assay is a qualitative and/or quantitative analysis of an unknown analyte. In one example, an assay can be a procedure that determines the concentration and sequences of DNA in a mixture. In another example, an assay can be an analysis of the type and concentrations of protein in an unknown sample.

Surface-based sensing assays are typically performed in environmental and biomedical diagnostics. The detection of analytes (targets) in a mixture is often implemented at a solid-liquid interface. Passive solid supports, which include glass substrates or polymer membranes, have probe molecules (i.e., "probes") immobilized on the surface of the solid supports that are used to bind the analytes of interest. Probes include, for example, proteins and nucleic acids. Probes are selected based on the analytes of interest such that there is a strong and specific interaction between a particular type of probe and a particular target.

More than one analyte can be detected using multiplexed detection. In multiplexed detection, different types of probes are arranged in an array on the surface of the solid supports. Each type of probe results in a strong and specific interaction with a different analyte of interest. For example, in DNA analysis, high density microarrays are used to examine gene expressions at the scale of entire genomes by simultaneously assaying mixtures derived from expressed mRNA against thousands of array sites, each bearing probes for a specific gene. Microarrays generally quantify target concentrations in relative terms, for example, in the form of a ratio to hybridization signal obtained using a reference target sample. Other biosensing applications are calibrated to provide absolute target concentrations.

Fluorescent-based detection is commonly used for quantifying the extent of probe-target binding in surface-based sensing assays. In fluorescent-based detection, a target is labeled with a fluorophore molecule, which can cause the target fluorophore to be fluorescent. Traditional microarray scanners include an excitation source, such as a laser, that emits light on the bound target fluorophores. This causes the target fluorophores to emit fluorescent light that is focused and collected (through a generally lossy optical path) onto a cooled charge-coupled device (CCD) or a photomultiplier tube (PMT). Optical filtering is typically used to improve the signal-to-noise ratio (SNR) by removing background light or reflected excitation light. In addition, the arrays are generally sensitive to particular fluorophore concentrations from $10^8$ to $10^{11}$ $cm^{-2}$.

Characteristic lifetimes are associated with each fluorophore. The lifetime is defined by the transient exponential fluorescent decay of the fluorophore once the excitation source is removed. The lifetime, which is typically on the order of nanoseconds for organic dyes, is characteristic of the dye and the environment, and can be used in addition to color and intensity for multiplexed detection. Quantum-dot fluorophores can have lifetimes exceeding 15 nanoseconds at the cost of slightly lower quantum yields. Fluorescent lifetime detection, for example, has been employed for capillary electrophoresis in both the time and frequency domain. Fluorescent lifetime is also sensitive to excited-state reactions, such as fluorescent resonance energy transfer (FRET), which allows for the detection of macromolecular associations labeled by two different fluorophores. For micro-arrays, FRET can be used to detect in situ real-time hybridization kinetics in which both the probe and target are fluorophore-labeled.

In most commercial time-resolved systems, PMT detectors use time-correlated single photon counting (TCSPC). In this case, sensitivity is limited by a dark count, which is typically about 400 Hertz (Hz). For a typical peak quantum efficiency of 25%, this corresponds to a detection limit of approximately $2 \times 10^5$ photons/$cm^2$ sec (i.e., $5 \times 10^{-7}$ lux) for an SNR of 20 decibels (dB). For an effective lifetime measurement, a detection limit of at least ten times this can be expected. The time resolution (as determined by the full width at half maximum (FWHM) of the impulse response of the PMT) is limited by jitter in the PMT and instrumentation, and can be less than 50 picoseconds (ps).

The response of the fluorophore is characterized by the absorption cross-section and quantum yield. Typical fluorophores have cross-sections between $2 \times 10^{-17}$ $cm^2$ and $8 \times 10^{-16}$ $cm^2$, corresponding to molar extinction coefficients between $\epsilon = 50,000$ $cm^{-1}M^{-1}$ and $200,000$ $cm^{-1}M^{-1}$. Typical fluorophores also have quantum yields ($\eta$) of between 0.05 and 1.0. For example, for $\eta = 0.5$ and $\epsilon = 50,000$ $cm^{-1}M^{-1}$, under steady-state illumination, a detection limit of $2 \times 10^6$ photons/$cm^2$ sec could correspond to surface detection limits down to $2 \times 10^2$ molecules/$cm^2$ with an excitation power of $10^{20}$ photons/$cm^2$ sec. Detection limits this low are said to characterize single-molecule detection capabilities. Actual detection limits are usually several orders of magnitude greater than this and are limited by background—either the effectiveness of optical filtering in removing the excitation wavelength or in removing stray fluorescence. Lower excitation power also results in higher detection limits.

Known surface-based sensing assays are typically provided on external, macroscopic instruments. Such instruments are often expensive, large, and complex.

Therefore, there is a need in the art to provide a low cost, compact, and integrated chip for surface-based sensing arrays that provides capabilities similar to those on the macroscopic instruments.

Accordingly, it is desirable to provide methods and systems that overcome these and other deficiencies of the prior art.

SUMMARY OF THE INVENTION

In accordance with the present invention, systems and methods are provided for providing time-resolved, time-gated fluorescent-based detection on an active complementary metal oxide semiconductor (CMOS) biosensor chip.

An active CMOS biosensor chip for fluorescent-based assays is provided that enables time-gated, time-resolved fluorescence spectroscopy. Analytes are loaded with fluorophores that are bound to probe molecules immobilized on the surface of the chip. Photodiodes and other circuitry in the chip are used to measure the fluorescent intensity of the fluorophore at different times. These measurements are then averaged to generate a representation of the transient fluorescent decay response of the fluorophores, which is unique to the fluorophores. This data can then be used for further analysis of the analytes.

In addition to its low-cost, compact form, the biosensor chip provides capabilities beyond those of macroscopic instrumentation by enabling time-gated operation for background rejection, easing requirements on optical filters, and by characterizing fluorescence lifetime, allowing for a more detailed characterization of fluorophore labels and their environment. The biosensor chip can be used for a variety of applications including biological, medical, and in-the-field applications. The biosensor chip can be used for DNA and protein microarrays where the biomolecular probe is attached directly to the chip surface. The biosensor chip can also be used as a general fluorescent lifetime imager in a wide-field or confocal microscopy system. For example, the biosensor chip can be used as an imager in a conventional widefield epifluorescent microscope for lifetime imaging.

According to one or more embodiments of the invention, a method is provided for operating an imager with time-resolved, time-gated fluorescent-based detection comprising: (a) receiving light from a fluorescent source on a complementary metal oxide semiconductor (CMOS) biosensor chip, wherein the fluorescent source is excited by an external pulsed excitation light source; (b) directing the light source to turn off after a first time period; (c) measuring a fluorescent light from the fluorescent source on the CMOS biosensor chip after a second time period measured from when the light source is directed to turn off; (d) repeating (a)-(c) a number of times; and (e) averaging results from each measuring. The biosensor chip can be used as a microarray or as an imager in a widefield epifluorescent microscope for lifetime imaging.

According to one or more embodiments of the invention, a system is provided for time-resolved, time-gated fluorescent-based detection comprising: an external pulsed excitation light source; and a complementary metal oxide semiconductor (CMOS) biosensor chip coupled to the light source, wherein the CMOS biosensor chip is operative to (a) direct the light source to turn on, (b) direct the light source to turn off after a first time period, (c) measure a fluorescent light from a fluorescent source on the CMOS biosensor chip after a second time period measured from when the light source is directed to turn off, (d) repeat (a)-(c) a number of times, and (e) average results from each measure. The CMOS biosensor chip can include at least one driver, at least one photodiode, processing circuitry (e.g., sample-and-hold circuitry, analog-to-digital converter, and accumulator), and control circuitry. The CMOS biosensor can also include delay circuitry. The biosensor chip can be used as a microarray or as an imager in a widefield epifluorescent microscope for lifetime imaging.

According to one or more embodiments of the invention, an apparatus is provided for time-resolved, time-gated fluorescent-based detection comprising: a first printed circuit board on which is mounted a pulsed excitation light source; a second printed circuit board on which is mounted a complementary metal oxide semiconductor (CMOS) biosensor chip; and at least one cable with a first connector attached to the first printed circuit board and coupled to the light source and a second connector attached to the second printed circuit board and coupled to the CMOS biosensor chip. The CMOS biosensor chip can be operative to measure a fluorescent decay response of at least one fluorescently labeled target, wherein the target is bound to a probe immobilized on the surface of the CMOS biosensor chip, and wherein the fluorescent decay response is measured a plurality of times at a time period measured from a time when the light source is turned off after a period during which the light source is turned on.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed. herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

These together with the other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

Various objects, features, and advantages of the present invention can be more fully appreciated with reference to the following detailed description of the invention when considered in connection with the following drawings, in which like reference numerals identify like elements.

FIG. 18 is a table illustrating a summary for the simulated read noise sources in accordance with an embodiment of the invention.

FIG. 19 is a table illustrating the sensor chip's specification and a summary of the measured performance of the chip in accordance with an embodiment of the invention.

DETAILED DESCRIPTION OF THE INVENTION

Figure 1:
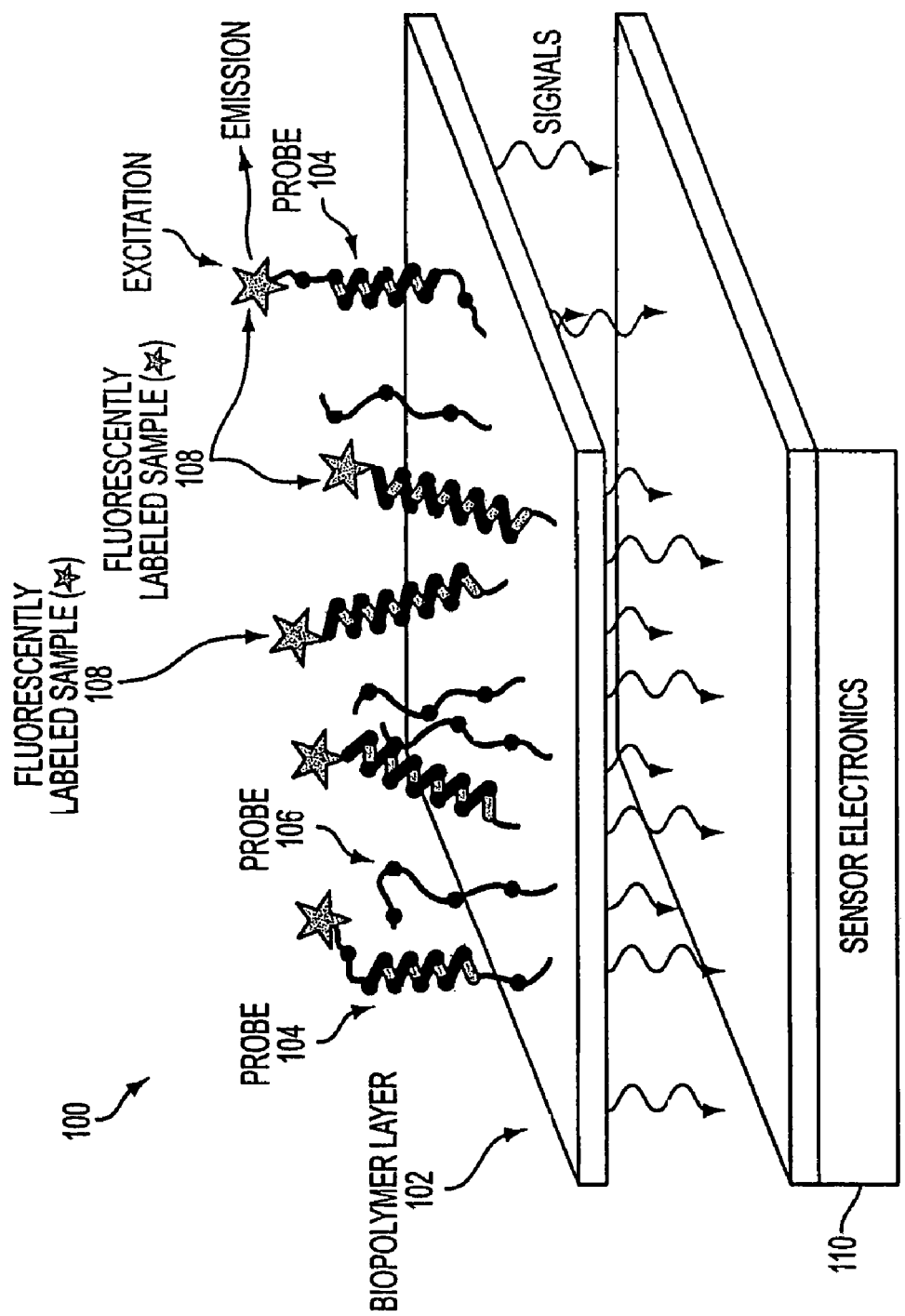
FIG. 1 is a block diagram of a sensor chip in accordance with an embodiment of the invention.

In the following description, numerous specific details are set forth regarding the systems and methods of the present invention and the environment in which such systems and methods may operate, etc., in order to provide a thorough understanding of the present invention. It will be apparent to one skilled in the art, however, that the present invention may be practiced without such specific details, and that certain features, which are well known in the art, are not described in detail in order to avoid complication of the subject matter of the present invention. In addition, it will be understood that the examples provided below are exemplary, and that it is contemplated that there are other systems and methods that are within the scope of the present invention.

In accordance with the present invention, an active complementary metal oxide semiconductor (CMOS) biosensor chip is provided for fluorescent-based detection. The present invention provides several advantages. The chip enables time-gated, time-resolved fluorescence spectroscopy. A time-gated operation provides additional background rejection and eases requirements on optical filters. In microarray applications, the chip also provides for probe molecules to be immobilized directly on the surface of the chip, thereby eliminating losses associated with the use of large and complex optical filters and also allows for efficient solid-angle collection. In addition, the ability to distinguish a fluorophore lifetime advantageously offers the potential to detect the presence of more than one fluorophore without the need for multiple optical filters.

Most time-resolved fluorescence systems rely on real-time photodetection with a photomultiplier (PMT) or avalanche photodiode (APD), which provides high gain and high sensitivity. Photodiodes, which are the photosensitive devices compatible with a CMOS process, do not have gain, but use averaging (e.g., in the form of integrating photocurrent onto a capacitor and averaging the results of multiple measurements) in order to achieve a high signal-to-noise ratio (SNR). When photodiode-based CMOS imagers combine long integration times with averaging, high sensitivity can be achieved.

High sensitivity can be achieved using a real-time detection application to extract a transient fluorescent decay response that follows the rapid turn-off of an excitation source (e.g., laser). Time-gating improves the signal-to-background ratio (SBR) of the detector by ensuring that the excitation source is turned off before collecting the photodiode response. Sub-sampling is used to achieve this real-time detection. The transient response is repeated a number of times. During each time, the integral of the photodiode current $i_{det}(t)$ is taken from a different starting time $(t_r)$ relative to the laser turn-off time, generating output $$\int_{tr}^{\infty} i_{det}(t)dt.$$

Sub-sampling preserves the sensitivity benefits of averaging (by integrating the photocurrent response) and reduces the bandwidth requirements on circuit components because the interval between repeated measurements can be used for data conversion, potentially overlapping with the integration of the next measurement. The result for a single starting time $(t_r)$ can also be repeated to improve the overall detection sensitivity. The photodiode current $i_{det}(t)$, which is directly proportional to the instantaneous fluorescence, can be generated by numerical differentiation.

FIG. 1 is a block diagram of a sensor chip 100 in accordance with an embodiment of the invention. Chip 100 includes a solid support such as a biopolymer layer 102 with probe molecules 104 and 106 (e.g., proteins and nucleic acids) immobilized on the solid support. Probes 104 and 106 are used to bind to different analytes in a mixture. For example, analytes 108 bind to probes 104 and not to probes 106. Chip 100 also includes sensor electronics 110 that detect and process signals generated by analytes 108. Although chip 100 is described herein primarily in the context of using a biopolymer layer 102 as a solid support and having two different probes 104 and 106 immobilized on the solid support for clarity, chip 100 may include any other suitable type of solid support and may have any suitable number of different types of probes for binding to different analytes.

Analytes may be labeled with fluorophore molecules. The fluorophores are originally in a ground state. During an excitation process, an excitation source (not shown) directs a light on chip 100. The excitation source can be any suitable pulsed excitation light source such as, for example, a pulse laser source. The pulse laser source can be any suitable laser source such as, for example, a gain switched or a mode-locked laser source. The fluorophores absorb the light, thereby increasing its energy levels until the fluorophores reach a high-energy excited state. Because the fluorophores are unstable in the high-energy excited state, during an excited lifetime process, the fluorophores lose some of its energy and adopt a lower energy excited state to become semi-stable. During an emission process, the fluorophores releases its excess energy by emitting light until the fluorophores return to the ground state.

Figure 2:
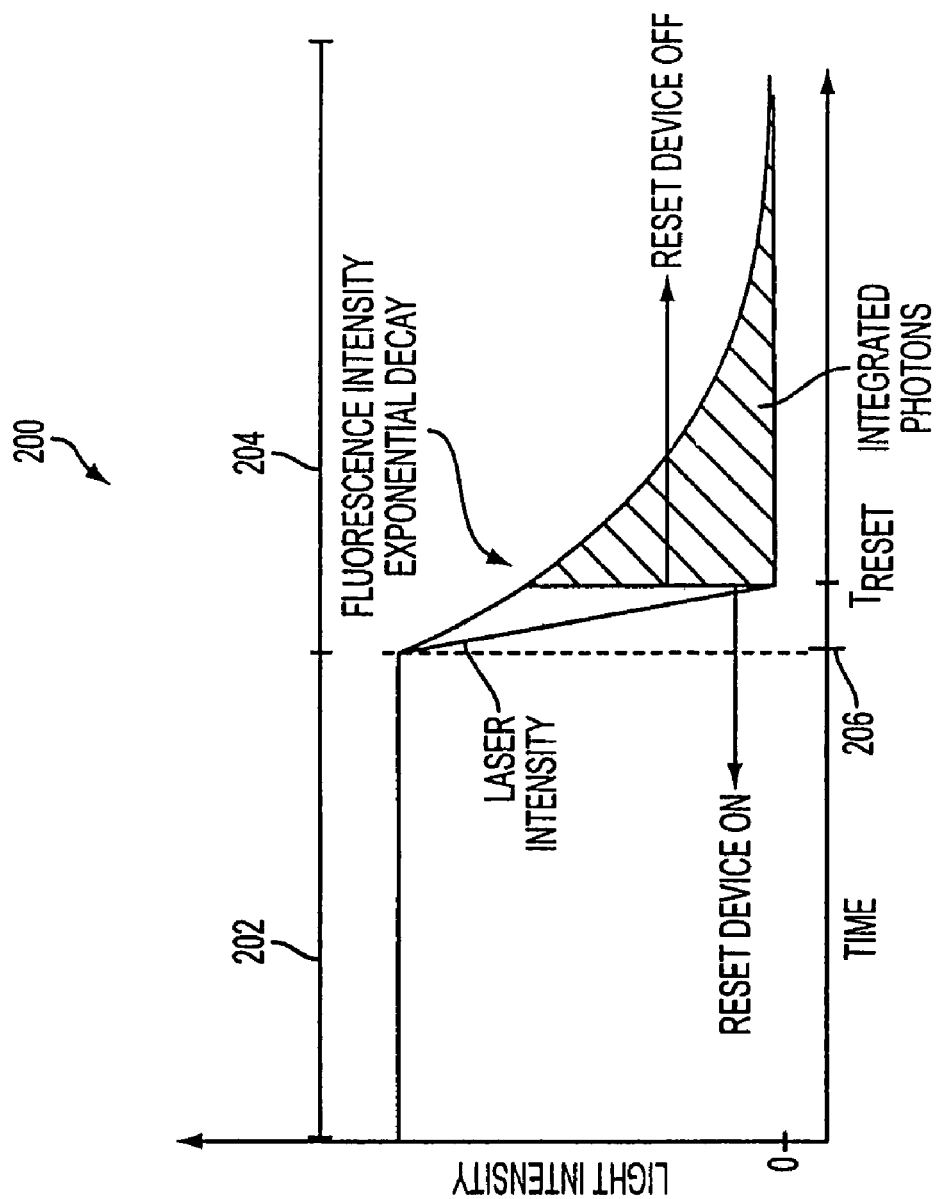
FIG. 2 is a timing diagram of time-resolved, time-gated fluorescent-based detection in accordance with an embodiment of the invention.

FIG. 2 is a timing diagram 200 of time-resolved, time-gated fluorescence detection illustrating a first time period 202 when an excitation source such as a laser is turned on and a second time period 204 when the laser is turned off. During time period 202, the laser emits a light, causing fluorophores in analytes 108 to absorb the light and to reach an excited state. The fluorescence intensity of the fluorophores is high. At time 206, the laser is turned off. During time period 204, the intensity of the fluorophores decays at a substantially exponential rate until the ground state is reached. In order to extract the fluorescent decay response, sub-sampling of the fluorescence intensity (which can be a measure of the photodiode current) from different starting times $t_r$ relative to time 206, can be measured. These measurements can be averaged to generate a value representing the area under the fluorescent decay response curve (i.e., the integral of the photodiode current).

Figure 3:
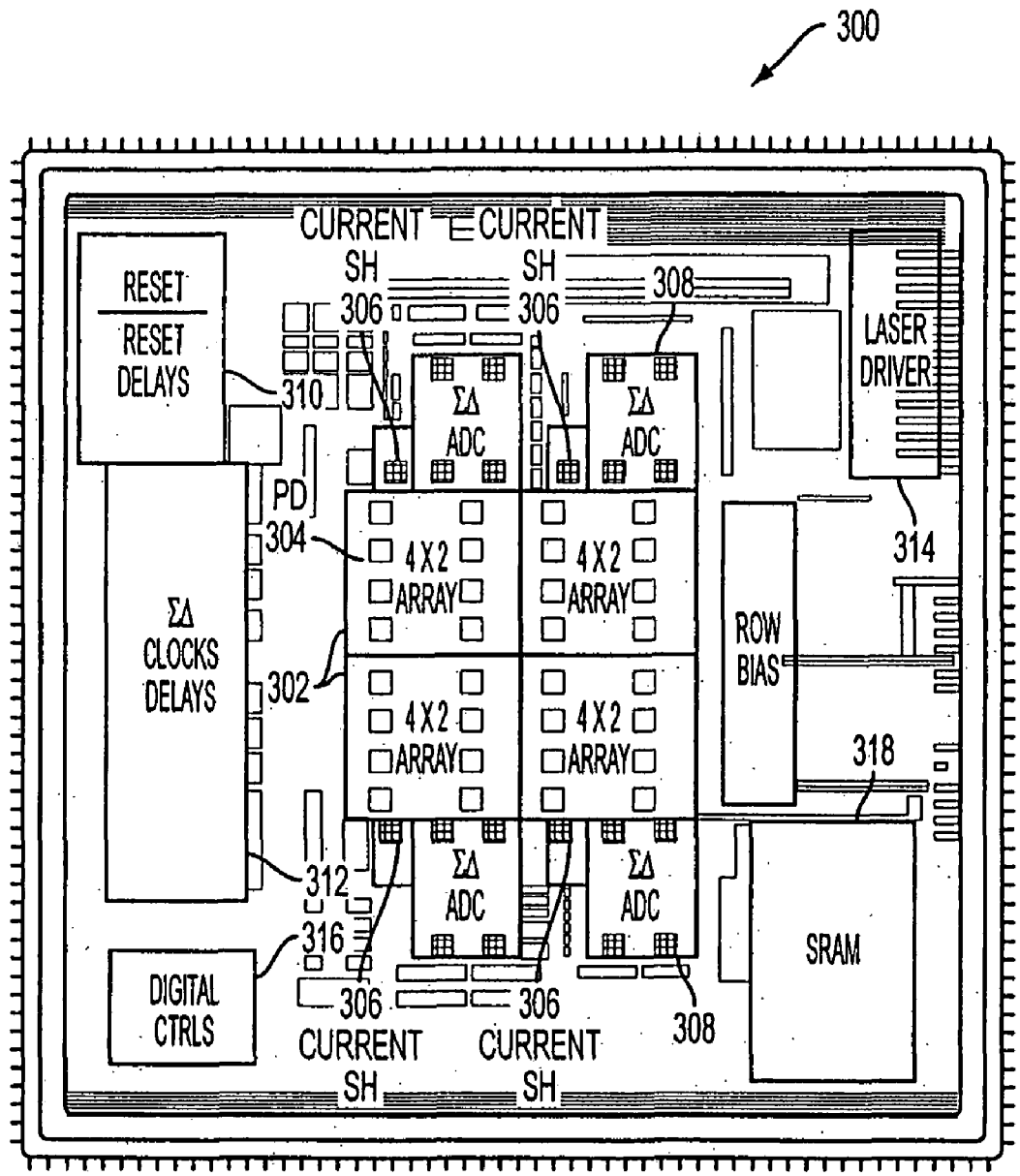
FIG. 3 is a die photograph of a sensor chip in accordance with an embodiment of the invention.

FIG. 3 is a die photograph of a sensor chip 300 in accordance with one embodiment of the invention. Chip 300 can be a 5 mm×5 mm CMOS biosensor chip fabricated in a mixed-signal 0.25 μm process. Chip 300 includes an 8×4 pixel array that is divided into four banks (e.g., each bank is arranged as a 4×2 array 302) of eight pixels (each having a photodiode) 304, four current sample-and-hold (SH) circuits 306, four current-mode ΣΔ analog-to-digital converters (ADCs) 308, reset delay circuitry 310, ΣΔ clocks delay circuitry 312, laser drivers 314, a digital controller 316, and a static random access memory (SRAM) 318. Laser drivers 314 control the operation of an excitation source such as a laser. When the laser driver 314 sends a signal to the laser indicating that the laser is to be turned off, reset delay circuitry 310 receives and delays a reset signal (and its complement signal) by a time $t_r$, which is measured relative to the timing of laser drivers 314. The delayed reset signal is sent to pixels 304 in arrays 302 (e.g., to pixel reset predrivers). Pixels 304 receive fluorescent light from the fluorophores, and, upon receiving the delayed reset signal, send as output currents reflecting the fluorescence intensity of the fluorophores. The output currents are time-multiplexed into four SH circuits 306, which sample the currents and hold the currents for a period of time. The sampled current from each SH circuit 306 is sent as input to a respective ΣΔ ADC 308, which converts the sampled current from an analog format to a digital format. ΣΔ ADC 308 is controlled by ΣΔ clocks delay circuitry 312. Digital results are stored in an on-chip memory such as SRAM 318. Digital controller 316, which can be configured externally with a serial bit stream, generates the clocks and control signals for ΣΔ ADCs 308, steps through the appropriate $t_r$ values, controls the storage of digital samples, and determines the laser pulse duration.

Although FIG. 3 is described herein as being a particular dimension fabricated on a particular process, with certain configurations of circuitry, any other suitable sizes, processes, and configurations of circuitry may be used.

Figure 4:
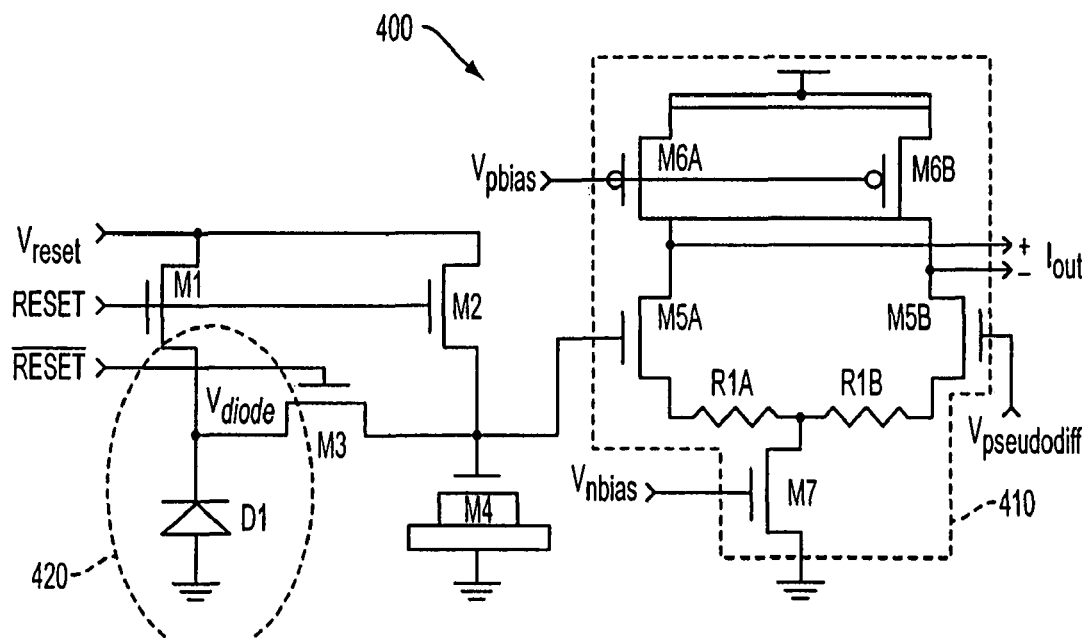
FIG. 4 is a schematic diagram of a pixel in accordance with an embodiment of the invention.

FIG. 4 is a schematic diagram 400 of each pixel 304. Circuit 400 includes two reset transistors M1 and M2, an isolation device M3, a storage capacitor M4, a transconductor 410, and a diode D1 420. Diode 420 can be an n-well/p-substrate photodiode. The photodiode in pixel 304 preferably includes an n-well guard ring to collect carriers generated by neighboring pixels 304. Transconductor 410 includes multiple transistors M5A, M5B, M6A, M6B, and M7, and two resistors R1A and R1B. Resistors R1A and R1B can be non-silicided polysilicon resistors that are used to linearize transconductor 410 through source degeneration. Transconductor 410 converts the voltage across storage capacity M4, which results from the integrated photocurrent, into a differential current ($I_{out}$) for subsequent current-mode data conversion. The transistors in diagram 400 may be any suitable type of transistor having any suitable size. In one embodiment, transistors M5A, M5B, and/or M7 can be large input n-field-effect transistors (n-FETs) (e.g., 4.32 mm/1 μm) to reduce 1/f noise and to improve matching performance.

During the reset phase, as determined by the RESET signal being set too high (i.e., binary "1"), transistor M3 is in an OFF state, effectively isolating M4 from DI. This reduces the capacitance on node $V_{diode}$ ($C_{pixel}$), which is the sum of the reverse-biased capacitance of D1 ($C_{diode}$) and the capacitances of M1 and M3 ($C_{M1,M3}$). For example, in an illustrative embodiment, $C_{diode}$ can be about 0.9 pF while $C_{M1,M3}$ can be about 10 pF. Transistor M1 is in an ON state, and is sized to provide a triode region resistance of $R_{reset}$ that allows $V_{diode}$ to be held within a particular voltage of $V_{reset}$, even for large photodiode currents associated with the excitation source. For example, in an illustrative embodiment, the 0.5 μm M1 reset device is 3 mm to provide a triode region resistance of $R_{reset}$ of about 1.8 Ω, which allows $V_{diode}$ to be held within 20 mV of $V_{reset}$ even for photodiode currents as large as 10 mA, which is the photocurrent associated with a 500 W/m² 635-nm laser. Isolation transistor M3 is sized such that it mitigates some of the voltage offset associated with charge-injection from transistor M1. For example, in an illustrative embodiment, M3 is 0.5 μm long and 1.5 mm wide.

Figure 5:
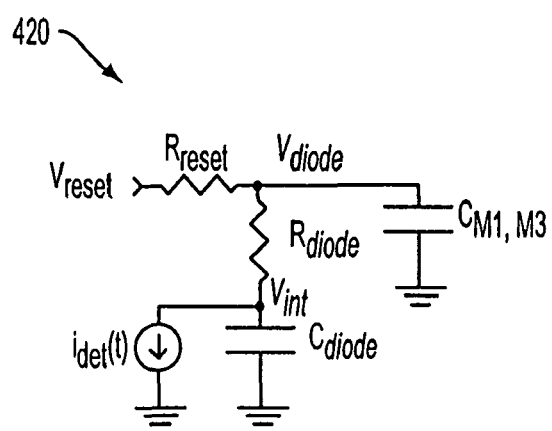
FIG. 5 is an equivalent circuit of the front-end of the pixel schematic shown in FIG. 4 in accordance with an embodiment of the invention.

FIG. 5 shows an equivalent circuit of the front-end of pixel diagram 400 (diode 420) during the reset phase. $R_{diode}$ is the parasitic resistance associated with the n-well bulk connection to diode 420. For example, in an illustrative embodiment, $R_{diode}$ can be about 1 kΩ, though the resistance may be reduced down to about 200 Ω through more careful design. The value of $R_{diode}$ limits the maximum sustainable photocurrent (e.g., to about 1 mA) before blooming can occur in diode 420 (i.e., the diode becomes forward biased because of the voltage drop across $R_{diode}$). Two time constants are associated with circuit 400: $\tau_{diode}=(R_{diode}+R_{reset})C_{diode}$ and $\tau_{M1,M3}=R_{reset}C_{M1,M3}$. For example, in an illustrative embodiment, $\tau_{diode}$ can be about 900 ps and $\tau_{M1,M3}$ can be about 20 ps. The bandwidth critical response of the pixel determined by these time constants is how quickly the internal diode voltage across $C_{diode}$ ($V_{int}$) can track the external diode voltage $V_{diode}$ during the reset phase. The laser diode pulse fall-time is preferably greater than both time constants for the pixel to track the photocurrent up to $t_r$. Transistor M3 acts to provide a larger capacitance for charge integration (e.g., 50 pF when reset is low) while removing the bulk of the capacitance (that of transistor M4) from the performance-limiting time constants.

The impulse response of the photodiode sensor, $h_{det}(t)$, when convolved with the fluorophore's response to the exci tation source (laser diode), $i_{em}(t)$, determines the signal output by the detector, $i_{det}(t)$:

$$i_{det}(t) = \int_{-\infty}^{\infty} h_{det}(t-t')i_{em}(t')dt' \qquad (1)$$

The pixel time constants and the fluorophore lifetime are reflected in $i_{det}(t)$. To be easily determinable, fluorophore lifetimes are preferably greater than the time constants associated with $h_{det}(t)$. To calculate an expression for $h_{det}(t)$ for the pixel, $i_{em}(t)$ can be set equal to $Q_o\delta(t)$. The pixel dynamics can be represented by the following system of differential equations:

$$C_{diode}\frac{dv_{int}}{dt} + \frac{v_{int} - v_{diode}}{R_{diode}} - Q_o\delta(t) = 0 \qquad (2)$$

$$C_{M1,M3}\frac{dv_{diode}}{dt} + \frac{v_{diode} - v_{int}}{R_{diode}} + \frac{v_{diode} - V_{reset}}{R_{reset}} = 0$$

Based on the assumption that $\tau_{M1,M3}/\tau_{diode} \ll 1$ for $t < t_r$ and $\tau_{M1,M3}/\tau_{diode} \gg 1$ for $t > t_r$, then for $t < t_r$:

$$v_{int}(t) = V_{reset} - \frac{Q_o}{C_{diode}} e^{-t/R_{diode}C_{diode}} \qquad (3)$$

with $V_{diode}(t) = V_{reset}$. Equation (3) shows that the pixel response time limits the ability of $V_{diode}$ to track $v_{int}$. Using these expressions to determine $v_{int}(t_r)$ and $V_{diode}(t_r)$ and using these as initial conditions for the solution of Equation 2 for $t > t_r$ yields the following expression:

$$v_{diode}(t) = V_{reset} + \frac{Q_o}{C_{diode} + C_{M1,M3}} e^{-\frac{t_r}{C_{diode}R_{diode}}} -$$

$$\frac{Q_o}{C_{diode} + C_{M1,M3}} e^{\frac{t_r}{C_{M1,M3}R_{diode}}} e^{-\left(\frac{C_{M1,M3}+C_{diode}}{C_{M1,M3}C_{diode}R_{diode}}\right)} \qquad (4)$$

Taking the limit as $t \to \infty$ of Equation (4) yields the following expression:

$$\tilde{v}_{diode}(t_r) = \frac{Q_o}{C_{M1,M3} + C_{diode}} e^{-t_r/R_{diode}C_{diode}} \qquad (5)$$

Equation (5) represents the total integrated voltage subsequently sensed by the pixel transconductor. The actual impulse response $h_{det}(t)$ is proportional to the derivative of $\tilde{v}_{diode}(t_r)$ with respect to $t_r$:

$$h_{det}(t) \cong \frac{-C_{pixtotal}}{Q_o} \frac{\partial \tilde{v}_{diode}(t)}{\partial t} = \frac{1}{R_{diode}C_{diode}} e^{-t/R_{diode}C_{diode}} \qquad (6)$$

Referring back to FIGS. 4 and 5, the pixel transconductor converts $V_{diode}$ to a differential current for subsequent current-mode data conversion. When used in this pseudo-differential manner, the transconductance is approximately:

$$g_{m,pixel} \approx \frac{-1}{\frac{2}{g_{m5}} + R_{1a}} \qquad (7)$$

where $g_{m5}$ is the transconductance of transistor M5. In an illustrative embodiment, $R_{1A}=R_{1B}=500\Omega$, yielding a measured transconductance of about 0.22 mS. The simulated 3 dB bandwidth is approximately 2.6 MHz. Large input nFETs (e.g., 4.32 mm/1 μm), transistors M5A and M5B, can be used to reduce 1/f noise and to improve matching performance. This, along with the large reset devices, limits the fill factor to approximately 13%. The overall gain of the pixel is 7.04× $10^{-7}$ μA per integrated electron from the photodiode.

Figure 6:
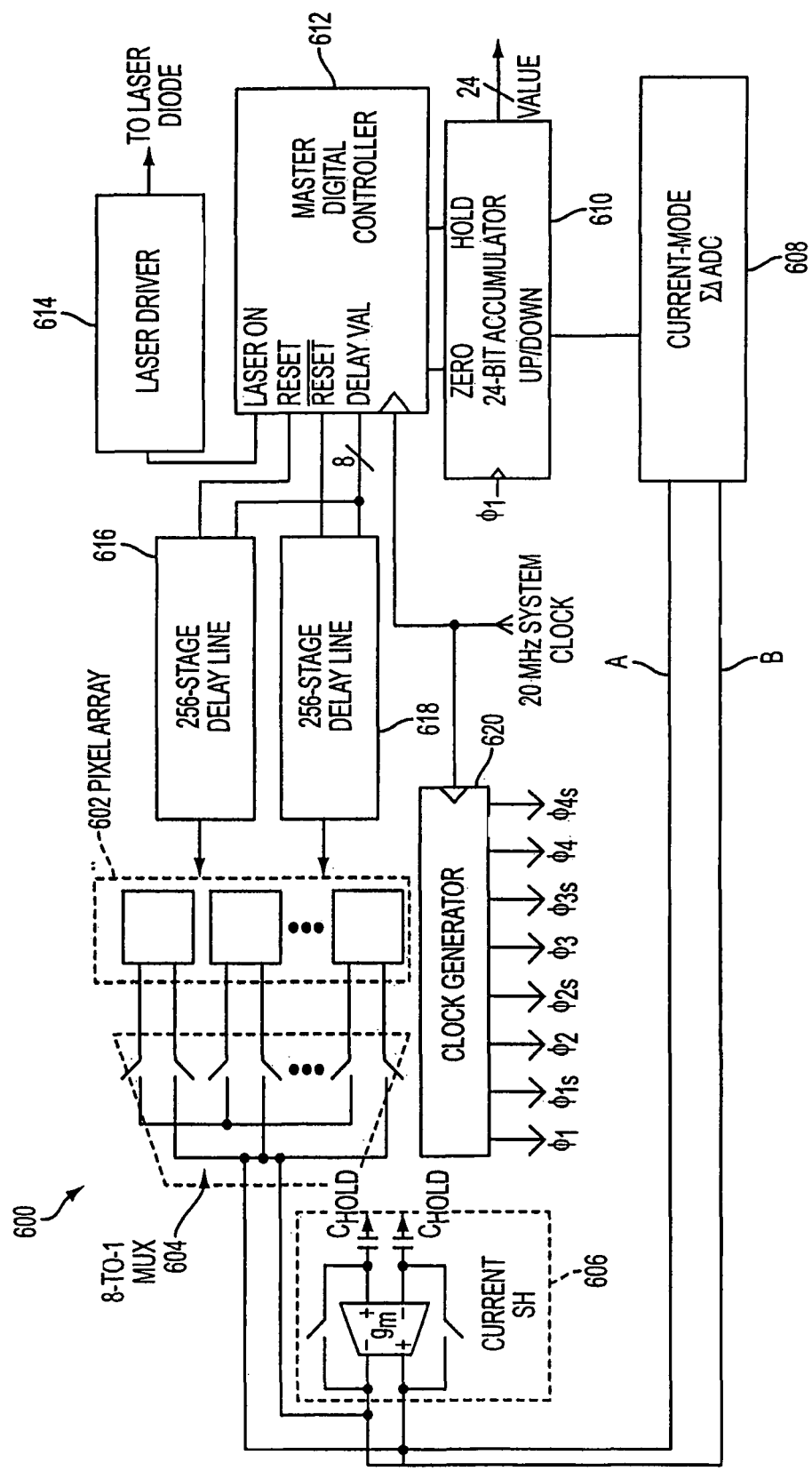
FIG. 6 is a simplified top-level schematic diagram of a sensor chip in accordance with an embodiment of the invention.

FIG. 6 is a simplified top-level schematic diagram 600 of a sensor chip. Circuit 600 includes the components similar to those illustrated in chip 300 (FIG. 3). Circuit 600 includes an array 602 having a number of pixels. In one embodiment, array 602 can be array 302 having eight pixels. Array 602 sends as output differential signal currents for each of the pixels, which are time-multiplexed using multiplexer 604 onto a current-mode SH element 606. In one embodiment, current-mode SH element 606 can be current SH circuit 306. Current-mode SH element 606 can include a differential transconductor with two feedback storage capacitors. The current-mode SH element 606 samples $g_{m,pixel}\tilde{v}_{diode}(t)$ for one of the multiplexed pixels.

The output of current-mode SH element 606 is continuously sampled by current-mode $\Sigma\Delta$ ADC 608. In one embodiment, current-mode $\Sigma\Delta$ ADC 608 can be $\Sigma\Delta$ ADC 308. Using a sampled version of the pixel current rather than sending the pixel current directly into $\Sigma\Delta$ ADC 608 advantageously reduces charge-injection and clock feed-through noise coupling back into array 602 through multiplexer 604.

Figure 7:
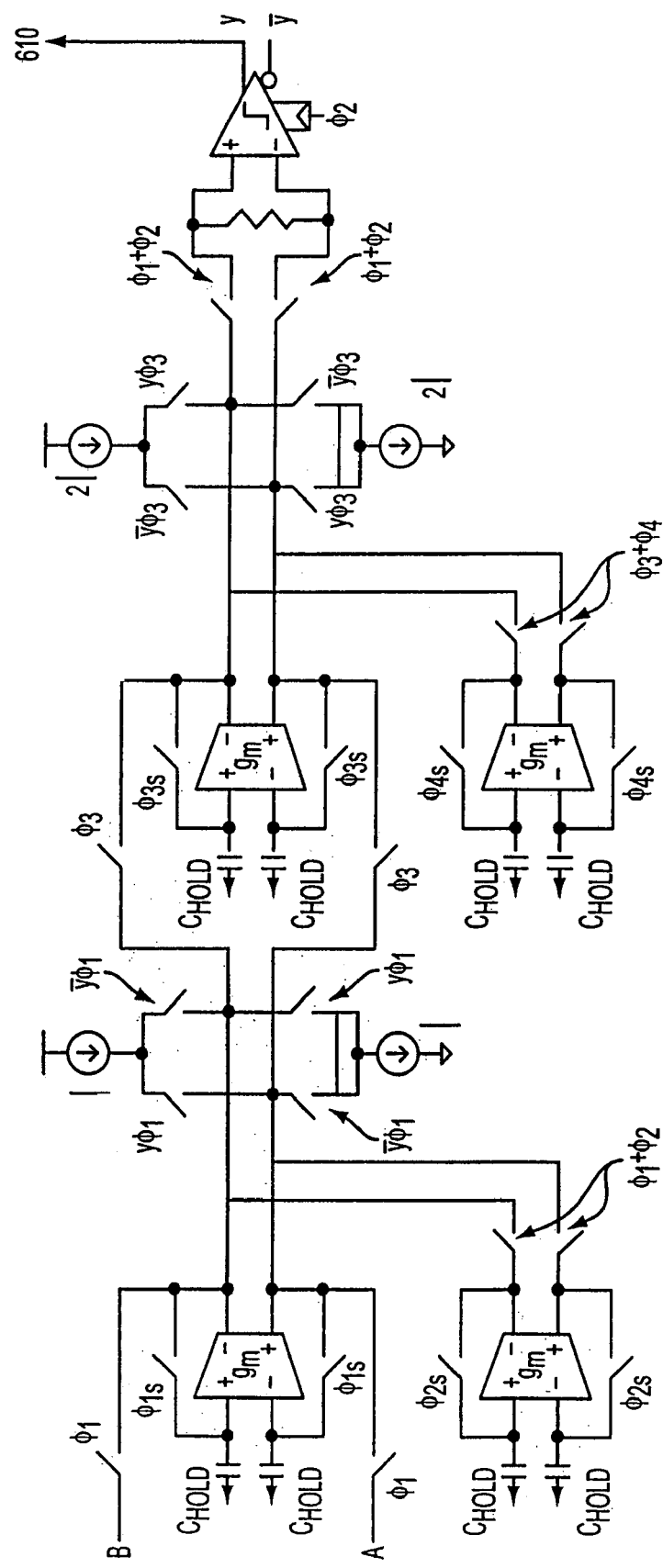
FIG. 7 is a schematic diagram of the current-mode $\Sigma\Delta$ analog-to-digital converter shown in FIG. 6 in accordance with an embodiment of the invention.

FIG. 7 shows a schematic diagram of $\Sigma\Delta$ ADC 608. $\Sigma\Delta$ ADC 608 can be a fully-differential, second-order, one-bit current-output circuit with a full-scale input level. For example, in an illustrative embodiment, for a full-scale input level of ±10 μA, the ADC can deliver a gain of 205 DN per μA of pixel current. The differential one-bit current-output DACs include two cascode current sources and a switch network. Pattern-dependent supply loading can be mitigated with a current-switch design by providing a fixed current (e.g., I=10 μA) across each DAC. Four, or any other suitable number of, non-overlapping clocks from clock generator 620 can be used to achieve a settling accuracy (e.g., of 12 bits) in the discrete-time current-copier integrators. In one embodiment, clock generator 620 can be $\Sigma\Delta$ clocks delay circuitry 312.

Figure 12:
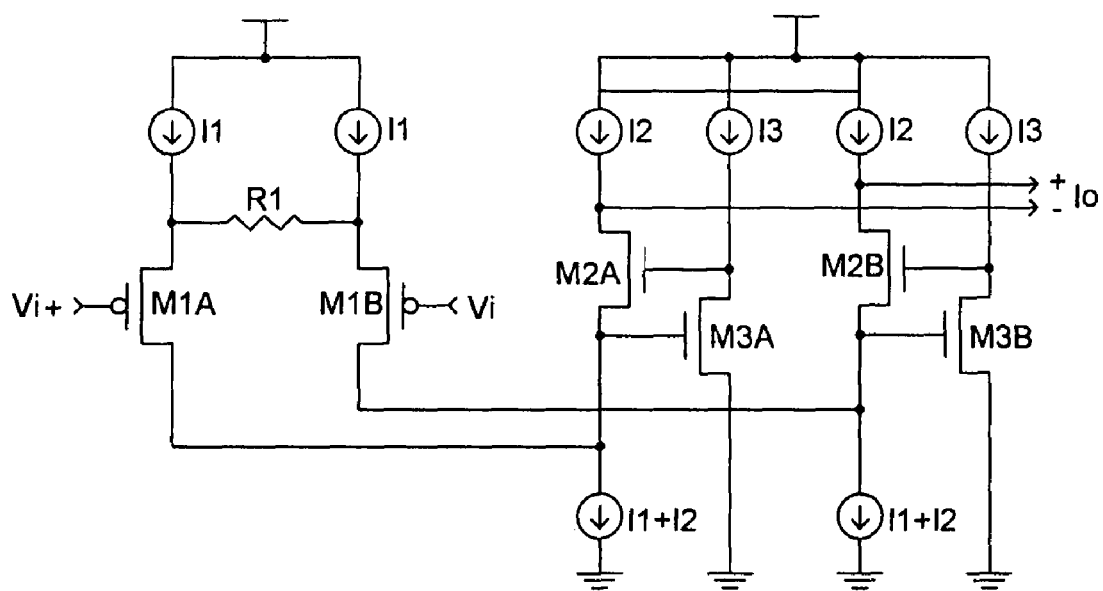
FIG. 12 is a schematic diagram of a transconductor used by the current-mode sample-and-hold (SH) circuit and the $\Sigma\Delta$ analog-to-digital converter circuits shown in the sensor chip in FIG. 6 in accordance with an embodiment of the invention.

In one embodiment, the transconductors in both current-mode SH element 606 and $\Sigma\Delta$ ADC 608 can use source-degenerating polysilicon resistors, which have a nominal transconductance. FIG. 12 illustrates a simplified schematic of a transconductor 1200 used in both elements 606 and 608. Transconductor 1200 includes a degeneration resistor R1 for linearization and devices M3A and M3B as an active cascode. Although not shown in FIG. 12, transconductor also includes triode region common-mode feedback devices for properly setting the common-mode level when the transconductor is used with fully differential feedback. In an illustrative embodiment, the DC transconductance ($g_m=I_o/(V_i^+ - V_i^-)$ ≈0.2 mS) is approximately 0.1 mS. The closed-loop bandwidth can be given by $$\frac{g_m}{2\pi(C_{hold}/2)} (\cong 120 \text{ MHz}),$$

where $C_{hold}$ (≅58 pF) is the holding capacitance, implemented as inversion-mode MOS capacitors. In this example, the bandwidth allows over 12 bits of settling accuracy to be achieved with four-phase nonoverlapping clocks operating with an 8 μs period.

The active cascode devices in the output stage of the transconductor can increase the performance of the circuit by mitigating the effects of finite device output conductance. The differential pair sees a very low input impedance ($R_i$) looking into the active cascode comprised of transistors M2 and M3:

$$R_i = \frac{r_{o2} + R_L/2}{1 + g_{m2}r_{o2} + g_{m2}g_{m3}r_{o2}r_{o3}} \quad (8)$$

This expression assumes a differential load resistance of $R_L$ loading the transconductor output and that the PMOS current sources have a high output resistance compared to the differential load. This low input resistance looking into the active cascode allows the majority of the current switched by the differential input pair to flow to the output instead of being shunted by the output conductance of the current source "I1+I2." The active cascode can also boost the output impedance ($R_o$) of the transconductor:

$$R_o = [r_{o2} + r_{eq} + g_{m2}r_{o2}r_{eq} + g_{m2}g_{m3}r_{o2}r_{o3}r_{eq}] \| r_{oI2} \quad (9)$$

where $r_{eq}$ is the parallel combination of the NMOS current source and impedance looking into the differential pair device M1 and $r_{oI2}$ is the output resistance of current source $I_2$. In this case, the larger the output impedance of the transconductor, the less significant the loading effects of the next stage become.

Referring back to FIG. 6, ΣΔ ADC 608 generates a one-bit "up" or "down" output that is sent as input to a 24-bit accumulator 610. In one embodiment, accumulator 610 can be a low-pass digital filter. The 12-bit (or other suitable number of bits) value generated by accumulator 610 after running ΣΔ ADC 608 for a number of cycles (e.g., 4096 cycles) has a relative accuracy of approximately 11 bits, limited by idle tones in ΣΔ ADC 608. The measured detrimental effect of idle tones is less than what behavioral modeling of ΣΔ ADC 608 predicts because of the dithering effect of noise at the input of the ΣΔ ADC 608 from current-mode SH element 606 and other analog noise signals in the ΣΔ ADC 608 loop.

Results from accumulator 610 are cached into an on-chip memory (e.g., SRAM 318). This eliminates the need for firing noisy off-chip drivers during repeated measurements. The outputs of the four accumulators 610 (each associated with a different array 302), are sent as input to a memory (e.g., SRAM) controller that coordinates writing this data to a single memory array. The address space of SRAM 318 is organized by sub-blocks and by which pixel within the sub-block is being written. SRAM 318 can be written in a single-pixel mode (e.g., a maximum of 2048 24-bit pixels values) or in a multiple-pixel mode (e.g., 64 values for each of 32 pixels). When measurements are completed and stored in SRAM 318, the entire contents of SRAM 318 can then be loaded off-chip.

In one embodiment, this can be performed in less than 310 μs. A single measurement can take 4097 ADC cycles to complete with one additional cycle used to allow SH element 606 to settle. Thus in this embodiment, one measurement on each of the four pixels can be repeated every 33 ms. Other suitable numbers of cycles and time periods can also be used in performing these measurements.

Circuit 600 also includes master digital controller 612, which drives both the array reset signal and the excitation source (e.g., a laser). In one embodiment, master digital controller 612 can be digital controller 316. Controller 612 can vary the skew between the signals of the reset signal and the laser to achieve time-resolved fluorescence detection. Laser driver 614 can include a variable width inverter with independent tunability of the pull-up and pull-down widths, selected digitally using control words (e.g., two seven-bit words). In one embodiment, laser driver 614 can be laser driver 314. Laser diodes with larger operating voltages can be accommodated by using thick oxide input/output (I/O) in the output circuitry of the laser driver. For example, for operating voltages greater than 2.5V, a thick oxide 3.3 V I/O can be used. This also allows the laser diode to tolerate overshoot at the near-end, which sometimes occurs as a result of reflections against the highly nonlinear load resistance turn-on characteristic of the laser diode.

The maximum current sourcing capability can be at any suitable voltage output that is sufficient to drive commercial laser diodes with certain optical outputs. Larger laser diodes can be sized such that they can be suitably driven by off-chip transmission lines in parallel. Pulse width and synchronization can be determined by controller 612.

For example, the maximum current sourcing capability at 2.7 V output can be greater than 130 mA, which is sufficient to drive commercial laser diodes with 50 mW of optical output. Large laser diodes with input capacitances of up to 40 pF can be driven by up to four off-chip 50-Ω transmission lines in parallel, resulting in near-end fall times of about 500 ps. The pulse width can be varied in 50 ns intervals up to 204.8 μs, but typically a pulse width of 300 ns is used.

Circuit 600 further includes programmable, variable delay lines 616 and 618 used to trigger the pixel reset predrivers in array 602. Delay line 616 delays the reset signal while delay line 618 delays the complement of the reset signal. The delay can be any suitable multiple of the period of the system clock combined with sub-clock period delay generation using an n-stage (e.g., n=256) inverter chain delay line. For example, for a system clock of 20 MHz, the delay can be any multiple of the system clock ($T_{cycle}$=50 ns) combined with any multiple of the stage delay $T_{delay}$ such that the reset time is $t_{reset}$=$nT_{cycle}$+$mT_{delay}$ (where n and m are positive integers). An n-bit multiplexer can be used to choose one of the phases in each delay line 616 and 618. The phases in each delay line 616 and 618 are preferably the complement of the other. Each delay line 616 and 618 and multiplexer is designed to limit mismatch between buffer stages that results from layout parasitics.

Large on-chip drivers for the reset and laser diode drivers (e.g., 616, 618, and 614) are designed to rapidly switch to achieve sufficient resolution for time-resolved detection. This can result in power-supply and substrate noise issues that may be a concern for the sensitive analog circuits of array 602 and ΣΔ ADC 608. Several techniques can be implemented to minimize these issues. For example, the slew rate of the reset signal can be limited to control noise generation. Array 602 and ΣΔ ADC 608 can be isolated from one another and other circuitry using a double guard ring. Supplies can be separated and decoupled on the chip. Data inputs to, and data outputs from, the chip can also be separated (e.g., all bias currents and voltages can sent as input into one side of the chip while all digital signals can be interfaced from another side of the chip).

Circuit read noise and photon shot noise determine the SNR and the dynamic range for the measurement of $\tilde{v}_{diode}(t)$. The read noise generally include four major components: the pixel reset noise, the pixel transconductor noise, the current-mode SH noise, and the quantization noise of the ADC. Averaging of repeated measurements can be used to reduce the first three read noise sources, thereby leaving the system noise floor determined by the quantization limit of the ADC. Simulated read noise sources are summarized in the table in FIG. 18.

Pixel reset noise. Referring to FIGS. 4-5, during the reset phase, two capacitors are typically reset: $C_{pixel}=C_{diode}+C_{M1}$, $M3$ and the sampling capacitance $C_{M4}$, which is determined by the gate capacitance of M4. In an illustrative embodiment, $C_{pixel}$ can be approximately 10.9 pF, while $C_{M4}$ can be approximately 30 pF. Long reset times are typically used to provide a steady-state system. As a result, the sampled noise voltage power on a capacitor C can be given by kT/C. The total mean-squared noise charge can be given by the following expression:

$$\overline{Q_{n,reset}^2} = \frac{kT}{C_1}C_1^2 + \frac{kT}{C_{M4}}C_{M4}^2 \text{ (e.g., } = 1.694 \times 10^{-31} C^2 \text{ at 300K)} \tag{10}$$

After reset, the switch M3 is turned on while switches M1 and M2 are turned off. The effective capacitance of the input node to the pixel transconductor can be given by $C_{pixtotal}=C_{pixel}+C_{M4}$ (e.g., ≈50 pF with the additional capacitance of the switch M3). Consequently, the mean-squared noise voltage at the input to the transconductor due to the reset devices can be given by the following expression:

$$\overline{V_{n,reset}^2} = \frac{\overline{Q_{n,reset}^2}}{C_{pixtotal}^2} \text{ (e.g., } = 6.776 \times 10^{-11} V^2 \text{ at 300K)} \tag{11}$$

Pixel transconductance noise. Referring to FIG. 4, the pixel transconductance noise is dominated by the thermal noise of the degeneration resistor and the channel thermal noise of transistors M5 and M6. The drain current noise power spectral density (PSD) of transistor M5 can be given by the following expression:

$$S_{n,M5} = 2qI_{DS5}\left(1+e^{-\frac{qV_{DS5}}{kT}}\right) + \frac{K_{M5}}{C_{ox}W_{M5}L_{M5}}\frac{g_{m5}^2}{f} \tag{12}$$

$K_{M5}$ is the 1/f noise constant for M5 and $I_{DS5}$ is the drain to source current of M5. Transistor M5 is biased in moderate inversion but close enough to weak inversion to justify the use of weak-inversion expressions for noise analysis. Similarly, the drain current noise PSD of transistor M6 can be given by the following expression:

$$S_{n,M6} = 4kT\frac{2}{3}g_{m6} + \frac{K_{M6}}{C_{ox}W_{M6}L_{M6}}\frac{g_{m6}^2}{f} \tag{13}$$

Transistor M6 can be biased near strong inversion so that this strong inversion noise expression can be used. Finally, the resistor current noise PSD of degeneration resistor $R_1$ can be given by the following expression:

$$S_{n,R1} = \frac{4kT}{R_1} \tag{14}$$

In this illustrative embodiment, using these expressions in simulation results in a total integrated input reference noise power of $2.915 \times 10^{-10}$ V$^2$. The 1/f noise sources of the pixel transconductor represent approximately 10% of the total noise over the integrated bandwidth.

Figure 13:
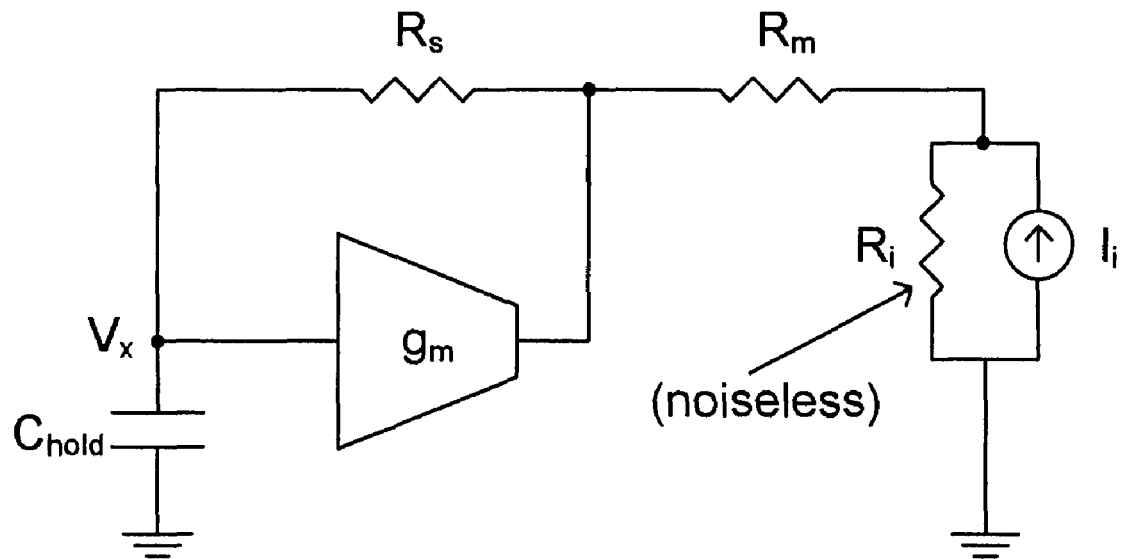
FIG. 13 is a schematic diagram of a half circuit used for analyzing the noise associated with current sampling by the current-mode SH circuit shown in the sensor chip in FIG. 6 in accordance with an embodiment of the invention.

Sample-and-hold noise. Additional noise is associated with current sampling by the current-mode SH. FIG. 13 shows a partial circuit 1300 used for this analysis. The noise voltage is stored at node $V_x$. $R_i$ is the output resistance of the driving stage (pixel transconductor), modeled by the current source $I_i$. Resistors $R_m$ and $R_s$ are the respective analog multiplexor switch on-resistance and current-mode SH feedback switch on-resistance. The transconductor is modeled as an ideal transconductor with transconductance $g_m$ and output resistance $r_o$. For large $R_i$, the sampled noise voltage on $V_x$ is dominated by the noise of $R_s$ and the transconductor equivalent output noise current. Assuming $r_o \gg R_s$, and $g_m r_o \gg 1$, the total integrated noise sampled on $V_x$ from the switch resistance $R_s$ can be given by the following expression:

$$\overline{V_{n,Rs}^2} \approx 2x\frac{kTR_s}{g_m r_o^2 C_{hold}} \tag{15}$$

This noise decreases as both the transconductance and holding capacitance of the current-mode SH increase. For large $r_o$, the total integrated noise due to the equivalent single-ended transconductor output current noise power spectral density $S_{n,gm}$ can be given by the following expression:

$$\overline{V_{n,gm}^2} \approx 2x\frac{S_{n,gm}}{g_m C_{hold}} \tag{16}$$

Once again, the circuit becomes less noisy when both the transconductance and holding capacitance increase. The total sampled noise on $V_x$, given by $\overline{V_{n,gm}^2}+\overline{V_{n,Rs}^2}$, when input-referred to $v_{diode}$ is denoted as $\overline{V_{n,currsh}^2}$ in the table in FIG. 18. This noise (e.g., $2.046 \times 10^{-9}$ V$^2$) can constitute more than two-thirds of the total read noise of the sensor.

Quantization noise. In an illustrative embodiment, the equivalent quantization noise ($\overline{V_{n,quant}^2}$) referred back to the pixel $v_{diode}$ node is $4.930 \times 10^{-10}$ V$^2$, assuming a 12-bit data conversion and a 30-mV swing on $\tilde{v}_{diode}(t)$. The total mean squared noise is 54 µV, which corresponds to approximately $3.74 \times 10^8$ photons/cm$^2$ for a quantum efficiency of 45% and capacitance $C_{pixtotal}$ of approximately 50 pF.

Unlike the shot noise analysis that is traditionally applied to imagers, the time-varying light intensity resulting from the fluorophore decay produces nonstationary shot noise statistics. The mean-square shot noise charge can be given by the following expression:

$$\overline{Q_{n,sh}^2} = \int_{t_r}^{\infty} qi_{em}(t)dt \tag{17}$$

Assuming that the fluorophore's response is a monoexponential decay represented by $i_{em}(t)=I_o e^{-t/\tau_{fluor}}$, where $\tau_{fluor}$ is the fluorophore's lifetime and $I_o$ is the initial intensity of the fluorescence decay, the integrated shot noise can be given by the following expression:

$$\overline{Q_{n,sh}^2} = q\tau_{fluor} I_o e^{-t_r/\tau_{fluor}} \tag{18}$$

This yields an input-referred mean-square voltage noise of $$\overline{V_{n,sh}^2} = \frac{\overline{Q_{n,sh}^2}}{C_{pixtotal}^2}.$$

Since the signal power is proportional to $e^{-2t_r/\tau}$, the SNR in the shot-noise-limited regime decreases with increasing $t_r$ as $e^{-t_r/\tau}$.

The time-gated behavior of the sensor provides for background rejection of the excitation source, even in the absence of optical filtering. In one embodiment, the background excitation reaching the sensor is assumed to have an exponential decay time given by $\tau_{diode}$, which is valid if $\tau_{diode}$ is much larger than the laser turn-off time. Furthermore, fluorophores excited during the turn-off transient can be ignored so that the fluorescent signal is characterized by a decay time given by the fluorescent lifetime $\tau_{fluor}$, which is valid if $\tau_{fluor} \gg \tau_{diode}$. $Q_{total}$ can represent the total charge generated in the sensor due to the pulsed excitation source in the absence of fluorophores. When the fluorophores are present, they absorb a fraction of the photons given by $\sigma c_{surface}$, where $\sigma$ is the absorption cross section and $c_{surface}$ is the surface concentration of fluorophores. The instantaneous currents generated in the sensor due to the excitation source (background) and the fluorophores (signal) can be represented by the following expressions:

$$I_{background}(t) = \frac{(1-\sigma c_{surface})Q_{total}}{\tau_{diode}} e^{-t/\tau_{diode}} \tag{19}$$

$$I_{signal}(t) = \frac{\eta\sigma c_{surface}}{\tau_{fluor}} e^{-t/\tau_{fluor}} \tag{20}$$

where $\eta$ is the quantum yield of the dye.

The signal-to-background ratio (SBR) can be given by the following expression:

$$SBR = \frac{\int_{t_r}^{\infty} I_{background}(t)dt}{\int_{t_r}^{\infty} I_{signal}(t)dt} = \frac{\sigma c_{surface}\eta}{1-\sigma c_{surface}} e^{-t_r \frac{\tau_{diode}-\tau_{fluor}}{\tau_{diode}\tau_{fluor}}} \tag{21}$$

Expressing this in units of decibels yields the following expression:

$$SBR_{dB} = t_r \frac{20}{\ln(10)} \frac{\tau_{diode}-\tau}{\tau_{diode}\tau} \tau_{diode}\tau + 20\log_{10}\left(\frac{\sigma c_{surface}\eta}{1-\sigma c_{surface}}\right) \tag{22}$$

$SBR_{dB}$ increases linearly with $t_r$, while the SNR decreases with increasing $t_r$. In one embodiment, an optimal value of $t_r$ for detection occurs when the SNR equals the SBR.

Figure 14:
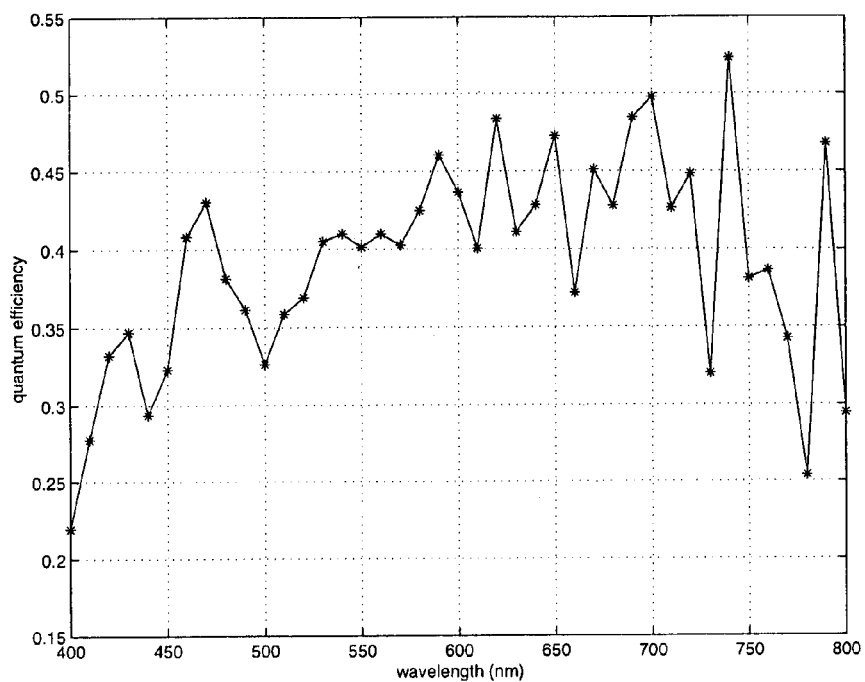
FIG. 14 is a chart illustrating the quantum efficiency of an n-well/p-substrate photodiode sensor as a function of the wavelength in accordance with an embodiment of the invention.

FIG. 14 shows the measured external quantum efficiency of the n-well/p-substrate photodiode as a function of the wavelength using a standard measurement set-up including a monochromator, integrating sphere, and calibrated photodetector. In an illustrative embodiment, peak quantum efficiencies in the range of 0.45-0.5 electrons/photons occur at wavelengths between 600-700 nm for the relatively deep diode junctions, suggesting a peak performance for dyes operating in this wavelength range. For example, the dye AlexaFluor 633 has a peak absorption at around 630 nm. The structure in the curve, particularly evident for the longer wavelengths, is due to interference effects in the dielectric stack.

Figure 8:
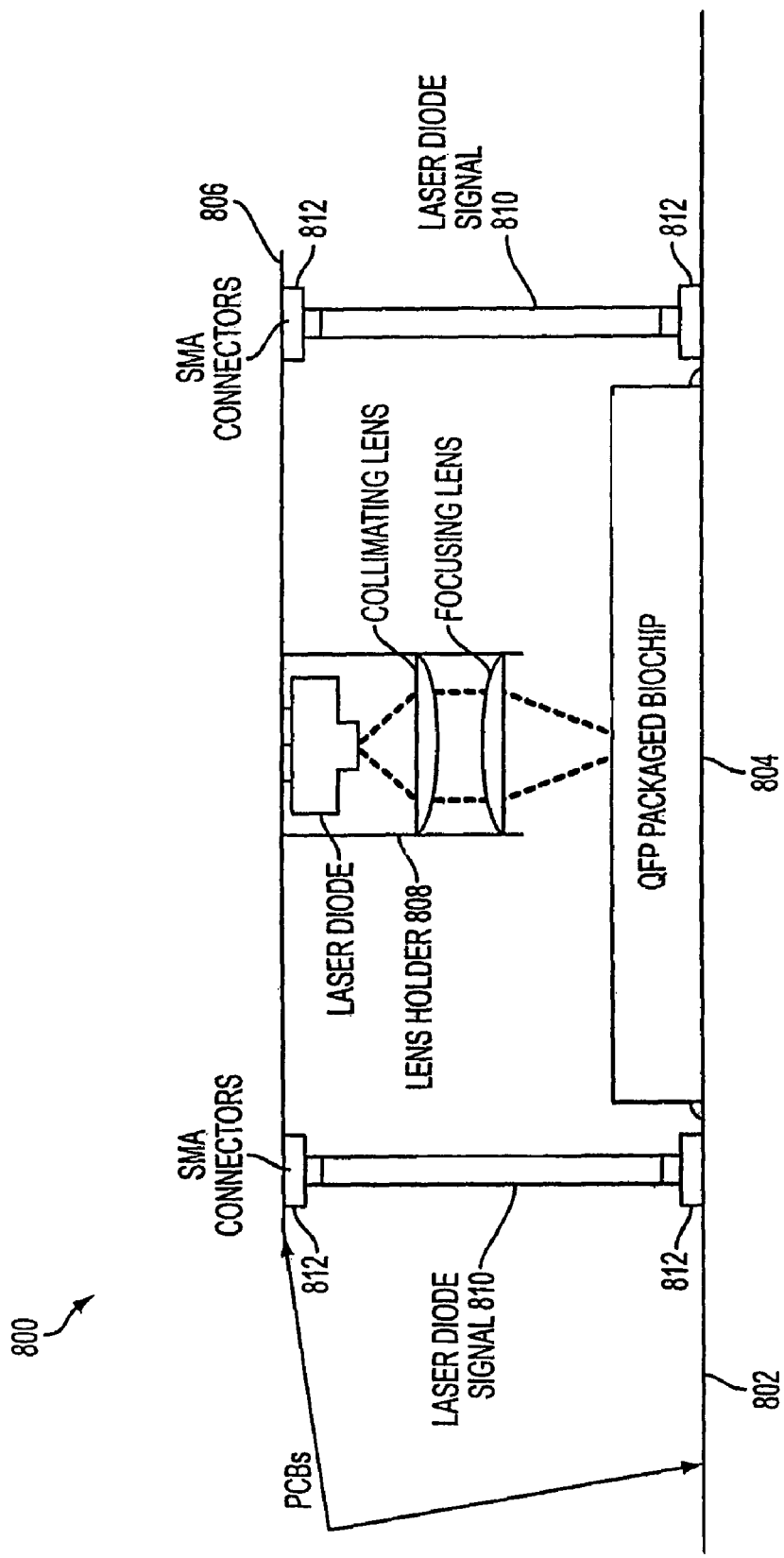
FIG. 8 is a block diagram of a fluorescent-based detection system in accordance with an embodiment of the invention.

FIG. 8 is a block diagram of is a block diagram of fluorescent-based detection system 800 in accordance with an embodiment of the invention. System 800 includes a first printed circuit board (PCB) 802. A biochip sensor, which can be packaged in a ceramic quad-flat-pack (QFP) package 804, is mounted on PCB 802. In one embodiment, the biochip sensor can include the circuitry shown in FIGS. 3-7. System 800 also includes a second PCB 806. Laser circuitry 808, which includes a laser diode, a lens holder, a collimating lens, and a focusing lens, is mounted on PCB 806. In one embodiment, the laser diode can be a 635 nm, 5 mW AlGaInP diode packaged in a 9 mm CAN style package. Alternatively, any other suitable diode can be used. PCB 806 is mounted over PCB 802 such that circuitry 808 can direct the light over analytes bound to the probes on the surface of biochip 804. Cables 810 with connectors 812 (e.g., SubMiniature version A or SMA connectors) are used to connect laser circuitry 808 to each of the laser drivers (e.g., laser drivers 314 or 614) on biochip 804.

Figure 15:
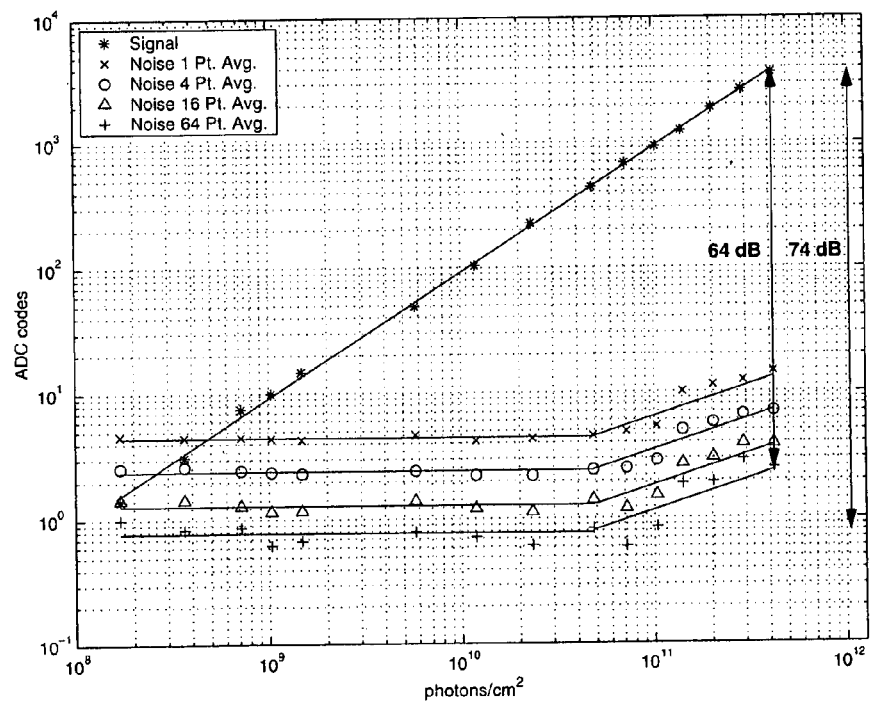
FIG. 15 is a chart illustrating the sensitivity of the sensor system in accordance with an embodiment of the invention.

Both the SNR, dynamic range (DR), and time-domain characterization can be performed with the sensor mounted with the laser diode and focusing optics as shown in FIG. 8. FIG. 15 characterizes the sensitivity of the sensor. In this case, in an illustrative embodiment, $t_r$ is chosen to position the end of the reset phase 8.5 ns before the laser diode turn-off, allowing the laser diode power to be directly integrated in the sensor. Neutral density filters can be used to vary the laser signal strength. While the natural density filters have transmission tolerances of about ±10%, the transmission of individual neutral density filters can be calibrated to remove this source of possible measurement error. As shown in FIG. 15, each point in the signal curve is the average of 2047 measurements. The signal curve shows good linearity over three orders of magnitude. The integral linearity is limited principally by the in-pixel transconductor to about nine bits. This can be calibrated to further improve linearity, leaving the system to perform at the limit of the ADV (e.g., 11 bits). The illumination is measured in units of photons/cm², with the imager measuring the integrated photon flux.

The noise curves of FIG. 15 can be generated by taking the average of blocks of N consecutive measurements in the original 2047 measurement dataset. The standard deviation of the floor (2047/N) averaged blocks of data is recorded as the-noise after averaging. The noise curves show the effect of averaging on reducing the noise floor of the system. The noise curves show the effect of averaging on reducing the noise floor of the system. Averaging 64 points yields a noise floor close to the 12-bit quantization noise limit of the system. At higher integrated photon flux, the noise curves acquire a one-half slope due to photon shot noise. The system shows a peak SNR, limited by photon shot noise, of 64 dB and dynamic range of 74 dB. The read noise floor of the sensor (without averaging) shown in FIG. 15 (e.g., 5×10⁸ photons/cm²) is slightly larger than that predicted by simulation (e.g., 3.74×10⁸ photons/cm²). This may be due to a slight underestimation of the read noise contribution of the pixel transconductor.

The measured dark current in the photodiode is approximately 2.31 pA, which corresponds to a dark current signal from the pixel transconductor of 10.4 µA per second of integration. The corresponding dark current shot noise level is approximately $10^{-3}$ digital numbers (DN) for 12-bit conversion, well below the quantization noise limit.

The results shown in FIG. 15 consider the excitation source (laser diode) the desired signal. Therefore, the dynamic range is the true dynamic range of the sensor. However, in a time-gated operation, if the excitation source is not turned completely off at $t_r$, the effective dynamic range can be reduced because the sensor will saturate at lower fluorescent signal levels.

Figure 16:
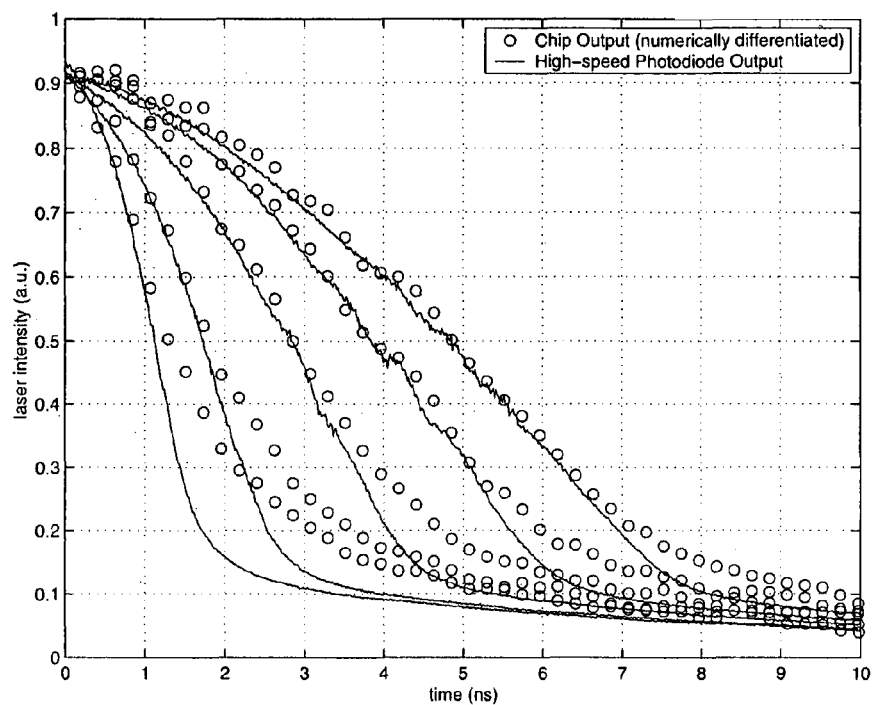
FIG. 16 is a chart illustrating the time-resolved detection of the laser turn-off edge in accordance with an embodiment of the invention.

FIG. 16 illustrates an illustrative embodiment of the time-domain response of the sensor in which $t_r$ is varied to reconstruct the actual turn-off transient of the laser. The solid line represents the output from a 12 GHz-bandwidth, New Focus 1577-A photodetector as measured by an Agilent 86100B oscilloscope. The circles show the numerically differentiated output of the sensor. The laser fall-time is varied from approximately 1 ns to 5 ns. For the fastest -fall times, the sensor output can lag the high-speed detector output due to the limitations of the $\tau_{diode}$ time constant described above.

The impulse response of the system is measured, for example, using a PiLas Picosecond Laser Diode System with a 635 nm laser diode head. The laser is capable of producing laser pulses of less than 40 ps FWHM with peak collimated beam power as high as 150 mW. The laser is triggered by the chip's laser driver output. The delay from the chip's laser driver signal to when the laser is actually fired can be controlled by varying the coaxial cable length carrying the trigger signal.

Figure 17:
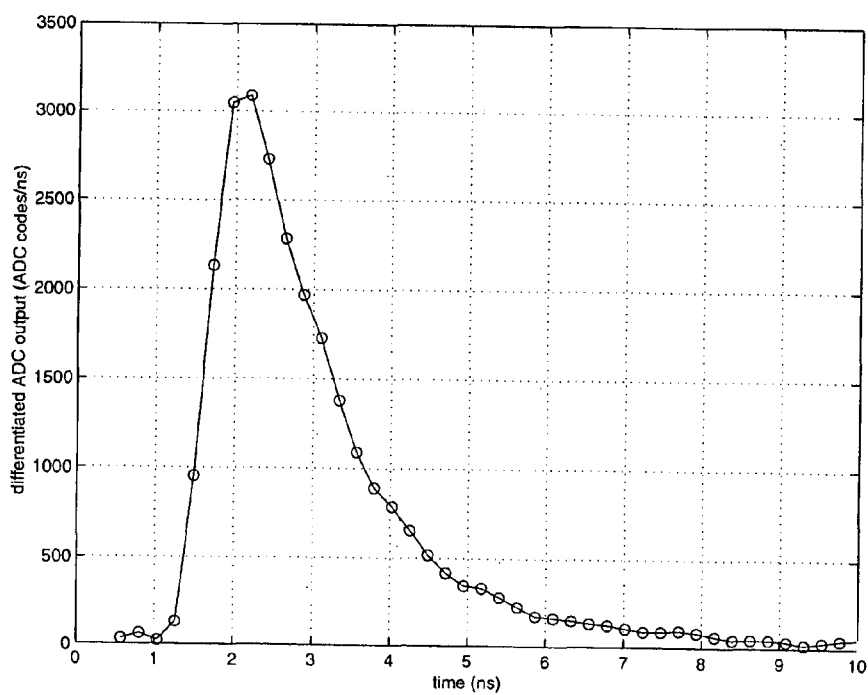
FIG. 17 is a chart illustrating the differentiated impulse response of the sensor system in accordance with an embodiment of the invention.

FIG. 17 shows the numerically differentiated ADC output of the system for an impulse excitation. In the illustrative embodiment, each time sample is measured 32 times and subsequently averaged to get the final waveform. The circuits depict the numerically differentiated output of the sensor. As described above, the system shows an exponential decay. An artifact of the 4-point numerical differentiation algorithm is apparent during the beginning of the pulse because the algorithm does not produce accurate results for a signal with such a high frequency edge and effectively low-pass filters it. The exponential decay has a time constant ($\tau_{diode}$) of 1.2 ns, suggesting a parasitic $R_{diode}$ resistance of approximately 1400 Ω.

For this value of $\tau_{diode}$, even for long-lifetime quantum-dot fluorophores, time-gating alone generally does not provide adequate background rejection for detection. To detect surface concentrations on the order of $10^8$ cm$^{-2}$, at least 160 dB of excitation rejection is needed. Even if $\tau_{diode}$ were reduced through design improvement to 500 ps, time-gating alone would not provide sufficient SBR. As a result, a thin-film optical filter can be added to the chip to provide sufficient SBR. For example, in one embodiment, an OD 5 23-layer $SiO_2/T_iO_2$ thin-film optical filter can be added to the chip. This filter, combined with time-gating, can thus result in more than 160 dB of background rejection being achieved.

In an illustrative embodiment of the invention described above, the CMOS fluorescence array sensor can achieve sensitivities of almost $c_{surface}=10^8$ molecules/cm$^2$, a dynamic range of 74 dB, and subnanosecond timing resolution, thereby resulting in a powerful, low-cost device for surface-based biomolecular assays.

Figure 9:
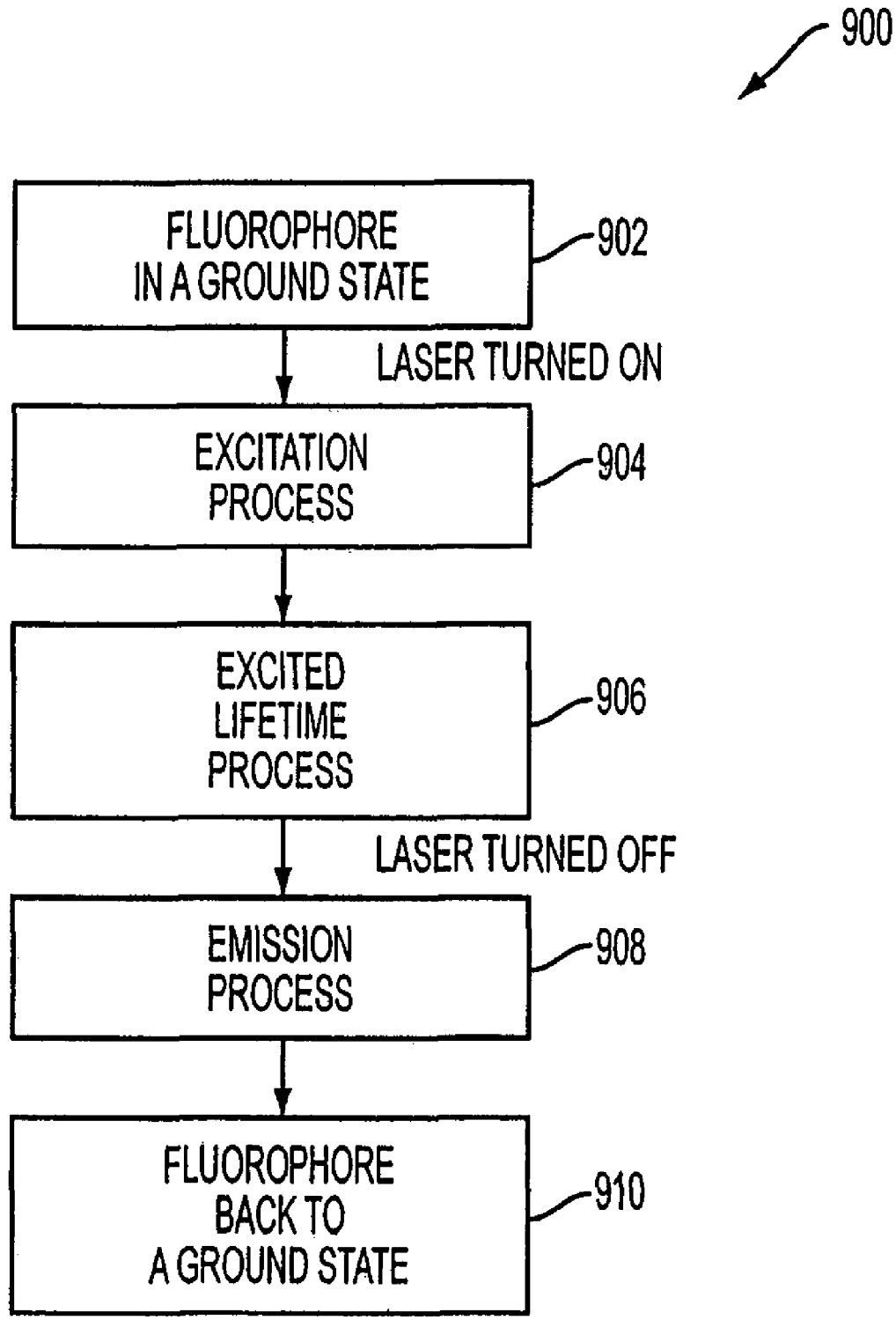
FIG. 9 is a flow chart illustrating different states of a fluorophore during fluorescent-based detection in accordance with an embodiment of the invention.

FIG. 9 is a flow chart illustrating different states of a fluorophore during fluorescent-based detection. Process 900 begins at step 902 where a fluorophore is in a ground state. When an excitation source such as a laser is turned on, process 900 moves to an excitation process at step 904. During the excitation process, a fluorophore absorbs light, increasing its energy level until it reaches a high energy excited state. Process 900 then moves to an excited lifetime process at step 906. During the excited lifetime process, the fluorophore loses some of its energy to adopt a lower energy excited state. When the laser is turned off, process 900 moves to an emission process 908. During the emission process, the fluorophores releases its excess energy by emitting light until the fluorophore returns to the ground state at step 910.

Figure 10:
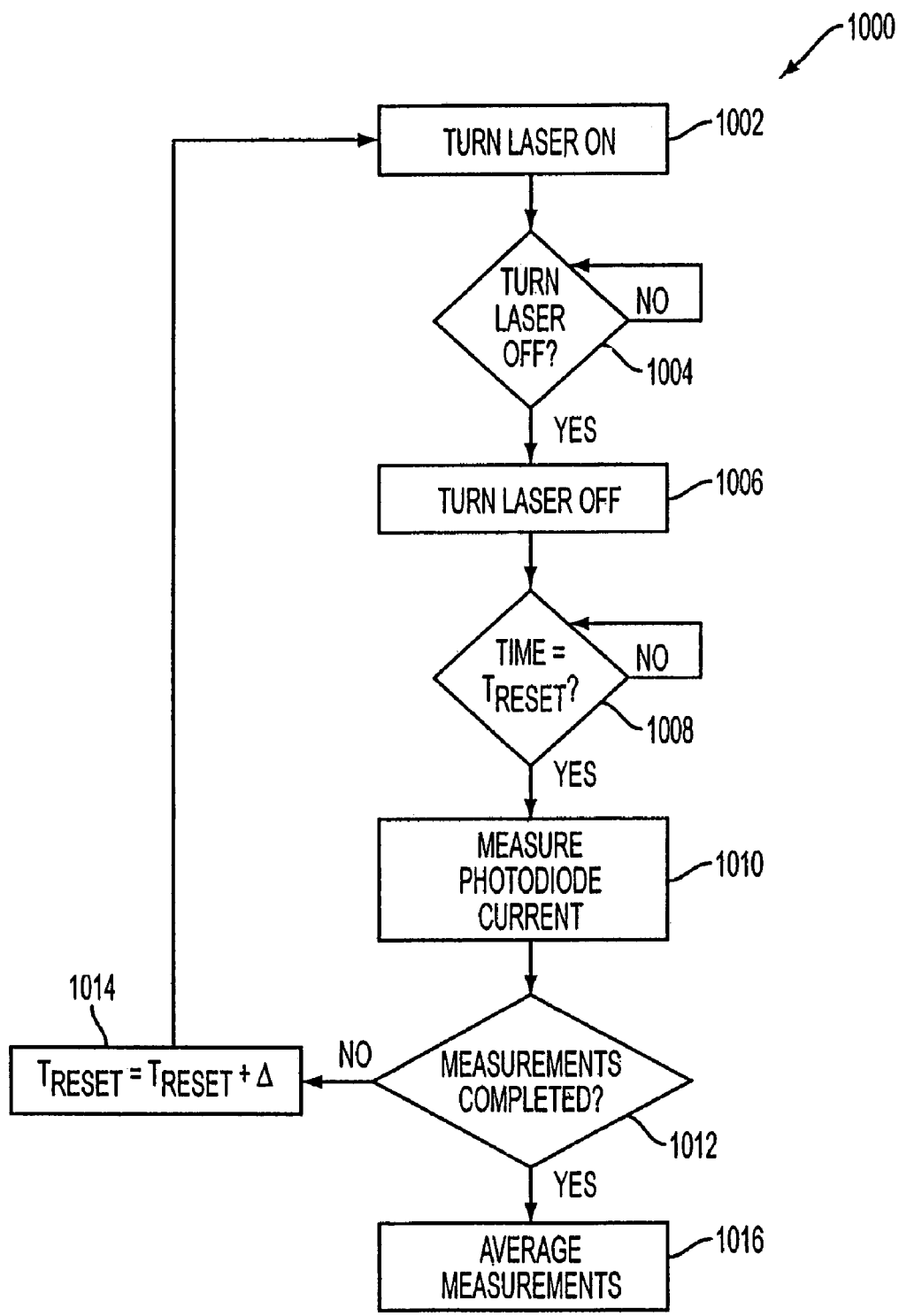
FIGS. 10-11 are flow charts illustrating processes for fluorescent-based detection in accordance with different embodiments of the invention.

FIG. 10 is flow chart illustrating a process 1000 for fluorescent-based detection in accordance with one embodiment of the invention. Process 1000 begins at step 1002 where an excitation source such as a laser is turned on. At step 1004, process 1000 determines whether the laser should be turned off. The laser may be programmed to be turned off after a predetermined time period, based on particular conditions (e.g., based on measurements in the array), or based on any other suitable measurement. When the laser is to remain on, process 1000 remains at step 1004. When the laser is to be turned off, process 1000 moves to step 1006 where the laser is turned off. The operation of the laser may be controlled by any suitable circuitry such as, for example, controllers 316 and 612 and/or laser drivers 314 or 614.

At step 1008, process 1000 determines whether the time that has elapsed, which is measured from the time that the laser is turned off, equals a particular rest time ($t_{reset}$). The reset time may be any suitable time and may be controlled by any suitable circuitry such as, for example, controllers 316 and 612 and/or delay lines 310, 616, and 618. When the reset time has not elapsed, process 1000 remains at step 1008. When the reset has elapsed, process 1000 moves to step 1010 where the photodiode current (in a pixel 304) is measured. At step 1012, process 1000 determines whether the measurements are completed. When the measurements are not completed, process 1000 moves to step 1014 where the reset time is changed (e.g., $t_{reset}$ is incremented by a particular amount Δ). Process 1000 then returns to step 1002 where the process is repeated so that another measurement of the photodiode current can be taken at a different reset time ($t_{reset}=t_{reset}+\Delta$).

Any suitable number of measurements may be taken using any suitable number of reset times ($t_{reset}$) such that the measurements can be used to uniquely identify the transient fluorescent decay response of a given fluorophore from other fluorophores. For each subsequent measurement, the reset time may change by the same predetermined incremental value. Alternatively, for each subsequent measurement, the rest time may change using different incremental values (e.g., as the elapsed time from the time that the laser is turned off increases, the incremental value may also increase). In another embodiment, the same reset time may be used for subsequent measurements to improve the overall detection sensitivity. The reset time may be set and/or changed by any suitable circuitry such as, for example, controllers 316 and 612 and/or delay lines 616 and 618.

When the measurements are completed at step 1012, process 1000 moves to step 1016 where the measurements are averaged to generate a representation of the transient fluorescent decay response of a particular fluorophore. These measurements can then be stored in an on-chip memory such as SRAM 306 or used for further processing of the data. Steps 1010, 1012, and 1016 may be performed using any suitable circuitry such as, for example, current SH elements 306 or 606, ΣΔ ADCs 308 or 608, and/or accumulator 610.

Figure 11:
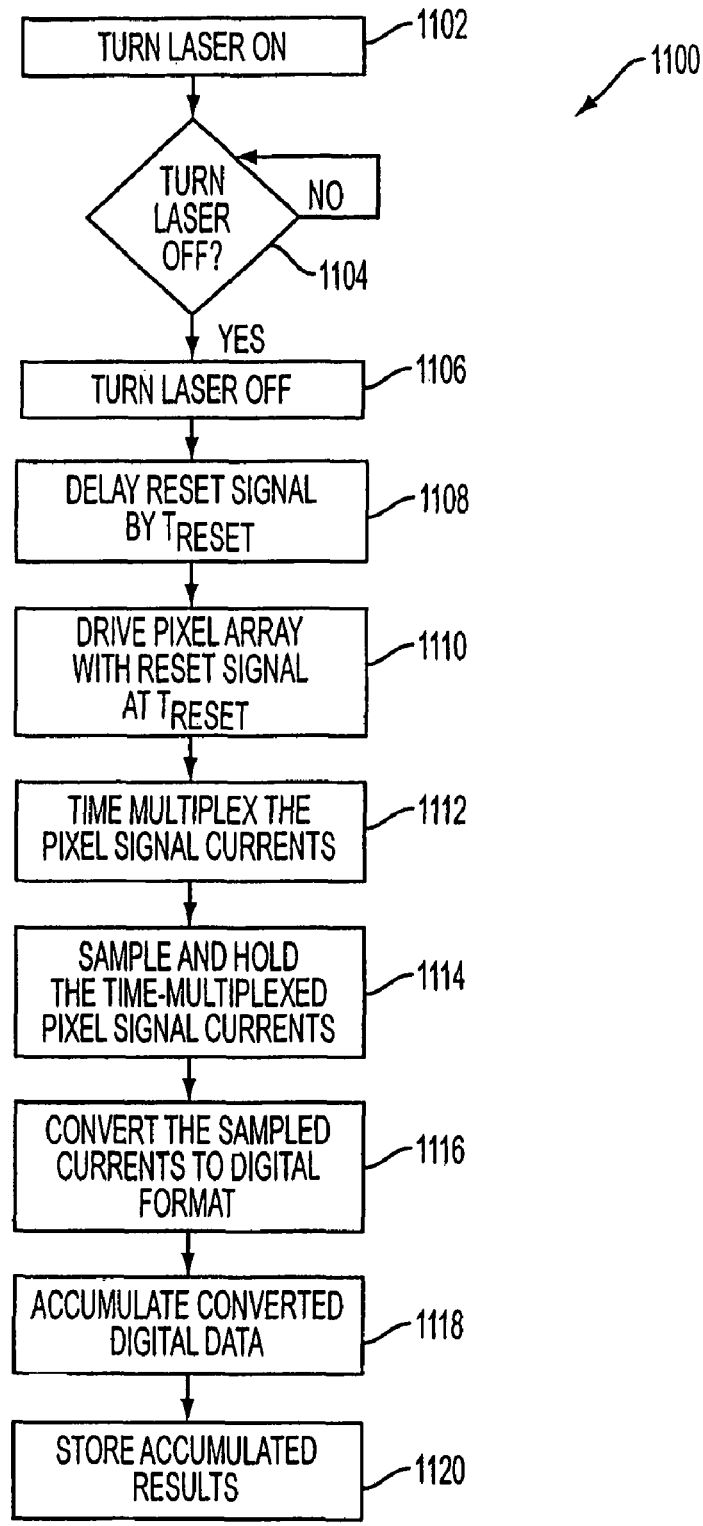

FIG. 11 is flow chart illustrating a process 1100 for fluorescent-based detection in accordance with another embodiment of the invention. Process 1100 begins at step 1102 where an excitation source such as a laser is turned on. At step 1104, process 1100 determines whether the laser should be turned off. The laser may be programmed to be turned off after a predetermined time period, based on particular conditions (e.g., based on measurements in the array), or based on any other suitable measurement. When the laser is to remain on, process 1100 remains at step 1104. When the laser is to be turned off, process 1100 moves to step 1106 where the laser is turned off. The operation of the laser may be controlled by any suitable circuitry such as, for example, controllers 316 and 612 and/or laser drivers 314 and 614.

At step 1108, a reset signal may be delayed prior to being sent to array 302 or 602. For example, the reset signal (and its complement signal) may be sent from controller 612 to delay line 616 (and 618) when the laser is turned off. Delay line 616 may delay the reset signal by a reset time ($t_{reset}$) (as described above in connection with FIG. 10). When the reset time has elapsed, process 1100 moves to step 1110 where the process drives pixel reset predrivers in array 302 or 602 with the delayed reset signal, causing the pixels in array 302 or 602 to output pixel signal currents. At step 1112, process 1100 time multiplexes the pixel signal currents. This may be performed using multiplexer 604. At step 1114, the time-multiplexed pixel signal currents are sampled and held for a period of time. This may be performed using current SH circuits 306 or 606. After the period of time, the sampled currents are converted from analog to digital format at step 1116. This may be performed using ΣΔ ADCs 308 or 608. At step 1118, process 1100 accumulates the converted data. This may be performed using accumulator 610. Although steps 1116 and 1118 are shown as separate sequential steps, ΣΔ ADCs 308 or 608 perform many cycles of converting sampled currents to digital format and sending the output to accumulator 610. Once all the data is accumulated, process 1100 moves to step 1120 where the accumulated results are stored. The results may be stored in an on-chip memory such as SPAM 306.

Process 1100 illustrates a process for fluorescent-based detection measured at one rest time ($t_{reset}$). Although not shown, process 1100 may be repeated a number of times. In one embodiment, the reset time in which fluorescent-based detection is measured may change with each subsequent measurement. In another embodiment, the reset time in which the fluorescent-based detection is measured may be the same with each subsequent measurement.

An active CMOS biosensor chip for fluorescent-based assays is provided that enables time-gated, time-resolved fluorescence spectroscopy. In addition to its low-cost, compact form, the biosensor chip provides capabilities beyond those of macroscopic instrumentation by enabling time-gated operation for background rejection, easing requirements on optical filters, and by characterizing fluorescence lifetime, allowing for a more detailed characterization of fluorophore labels and their environment. The biosensor chip can be used for a variety of applications including biological, medical, and in-the-field applications. The biosensor chip can be used for DNA and protein microarrays where the biomolecular probe is attached directly to the chip surface. The biosensor chip can also be used as a general fluorescent lifetime imager in a wide-field or confocal microscopy system. For example, the biosensor chip can be used as an imager in a conventional widefield epifluorescent microscope for lifetime imaging.

It is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods, and systems for carrying out the several purposes of the present invention.

Although the present invention has been described and illustrated in the foregoing exemplary embodiments, it is understood that the present disclosure has been made only by way of example, and that numerous changes in the details of implementation of the invention may be made without departing from the spirit and scope of the invention.

What is claimed is:

1. A method for operating an imager with time-resolved, time-gated fluorescent-based detection comprising:
   (a) receiving light from a fluorescent source on a surface layer of a complementary metal oxide semiconductor (CMOS) biosensor chip, wherein the fluorescent source is excited by an external pulsed excitation light source;
   (b) directing the light source to turn off after a first time period;
   (c) measuring a fluorescent light from the fluorescent source on the surface layer of the CMOS biosensor chip after a second time period measured from when the light source is directed to turn off;
   (d) repeating (a)-(c) a number of times; and
   (e) averaging results from each measuring.

2. The method of claim 1 further comprising measuring the fluorescent light with a photodiode.

3. The method of claim 1 wherein the CMOS biosensor chip is used as a microarray, in which the measuring comprises:
   immobilizing a probe on the surface of the CMOS biosensor chip;
   binding a fluorescently labeled target to the probe; and
   detecting the fluorescent light from the fluorescently labeled target.

4. The method of claim 1 wherein the CMOS biosensor chip is used as an imager in a widefield epifluorescent microscope for lifetime imaging.

5. The method of claim 1 wherein the second time period changes with each subsequent measuring.

6. The method of claim 1 wherein the second time period is the same with each subsequent measuring.

7. The method of claim 1 wherein the measuring comprises:
   driving a photodiode with a reset signal at the end of the second time period;
   receiving an integrated photocurrent across the photodiode;
   sampling the integrated photocurrent;
   converting the sampled integrated photocurrent from an analog format to a digital format; and
   averaging the converted integrated photocurrent.

8. A system for time-resolved, time-gated fluorescent-based detection comprising:
   an external pulsed excitation light source; and
   a complementary metal oxide semiconductor (CMOS) biosensor chip coupled to the light source, wherein the CMOS biosensor chip is operative to:
   (a) direct the light source to turn on,
   (b) direct the light source to turn off after a first time period,
   (c) measure a fluorescent light from a fluorescent source on a surface layer of the CMOS biosensor chip after a second time period measured from when the light source is directed to turn off, (d) repeat (a)-(c) a number of times, and (e) average results from each measure.

9. The system of claim 8 wherein the CMOS biosensor chip comprises:

at least one driver operative to direct the light source to turn on and off;

at least one photodiode operative to receive the fluorescent light;

processing circuitry operative to measure the fluorescent light and average results from each measure; and control circuitry operative to control the operation of the driver, the photodiode, and the processing circuitry.

10. The system of claim 9 further comprising delay circuitry operative to delay a reset signal by the second time period, wherein the output of the delay circuitry is used to time-gate the integration of photocurrent from the photodiode.

11. The system of claim 9 wherein the processing circuitry further comprises:

sample-and-hold circuitry operative to sample the integrated photocurrent from the photodiode;

an analog-to-digital converter operative to convert the integrated photocurrent from an analog format to a digital format; and an accumulator operative to average the converted integrated photocurrent.

12. The system of claim 8 wherein the second time period changes with each subsequent measuring.

13. The system of claim 8 wherein the second time period is the same with each subsequent measuring.

14. The system of claim 8 wherein the light source is a laser.

15. The system of claim 14 wherein the laser comprises a laser diode, a collimating lens, and a focusing lens held by a lens holder.

16. The system of claim 8 further comprising:

a first printed circuit board on which is mounted the light source;

a second printed circuit board on which is mounted the CMOS biosensor chip; and at least one cable with a first connector attached to the first printed circuit board and coupled to the light source and a second connector attached to the second printed circuit board and coupled to the CMOS biosensor chip.

17. The system of claim 8 wherein the CMOS biosensor chip is a ceramic quad-flat-pack packaged biochip.

18. The system of claim 8 wherein the CMOS biosensor chip is used as a microarray, in which the CMOS biosensor chip that is operative to measure the fluorescent light is further operative to:

immobilize a probe on the surface of the CMOS biosensor chip;

bind a fluorescently labeled target to the probe; and detect the fluorescent light from the fluorescently labeled target.

19. The system of claim 8 wherein the CMOS biosensor chip is used as an imager in a widefield epifluorescent microscope for lifetime imaging.

20. Apparatus for time-resolved, time-gated fluorescent-based detection comprising:

a first printed circuit board on which is mounted a pulsed excitation light source;

a second printed circuit board on which is mounted a complementary metal oxide semiconductor (CMOS) biosensor chip; and at least one cable with a first connector attached to the first printed circuit board and coupled to the light source and a second connector attached to the second printed circuit board and coupled to the CMOS biosensor chip.

21. The apparatus of claim 20 wherein the CMOS biosensor chip is operative to measure a fluorescent decay response of at least one fluorescently labeled target, wherein the target is bound to a probe immobilized on the surface of the CMOS biosensor chip, and wherein the fluorescent decay response is measured at a plurality of different time periods measured from a time when the light source is turned off after a period during which the light source is turned on.

22. The apparatus of claim 21 wherein the CMOS biosensor chip is further operative to average the fluorescent decay response measured at the plurality of different time periods.

23. The apparatus of claim 20 wherein the CMOS biosensor chip is operative to measure a fluorescent decay response of at least one fluorescently labeled target, wherein the target is bound to a probe immobilized on the surface of the CMOS biosensor chip, and wherein the fluorescent decay response is measured a plurality of times at a time period measured from a time when the light source is turned off after a period during which the light source is turned on.

24. The apparatus of claim 23 wherein the CMOS biosensor chip is further operative to average the fluorescent decay response measured at the plurality of times.

25. The apparatus of claim 20 wherein the CMOS biosensor chip is used as a microarray.

26. The apparatus of claim 20 wherein the light source is a laser.

* * * * *

UNITED STATES PATENT AND TRADEMARK OFFICE
CERTIFICATE OF CORRECTION

PATENT NO. : 7,738,086 B2  Page 1 of 1
APPLICATION NO. : 11/800468
DATED : June 15, 2010
INVENTOR(S) : Kenneth L. Shepard et al.

It is certified that error appears in the above-identified patent and that said Letters Patent is hereby corrected as shown below:

On column 1, lines 20-24:

Change "This invention was made with United States Government support under National Science Foundation Grant No. BES-0428544 and National Institutes of Health Grant No. HG003089. The United States Government may have certain rights in this invention." to --This invention was made with government support under National Science Foundation Grant No. BES-0428544 and National Institutes of Healthy Grant No. HG003089. The government has certain rights in the invention.--

Signed and Sealed this
Twenty-ninth Day of January, 2013

David J. Kappos
*Director of the United States Patent and Trademark Office*